US008183345B2

(12) United States Patent
Fay et al.

(10) Patent No.: US 8,183,345 B2

(45) Date of Patent: May 22, 2012

(54) RECOMBINANT FACTOR VIII HAVING REDUCED INACTIVATION BY ACTIVATED PROTEIN C

(75) Inventors: Philip J. Fay, Pittsford, NY (US); Hironao Wakabayashi, Rochester, NY (US); Fatbardha Varfaj, San Francisco, CA (US)

(73) Assignee: University of Rochester, Rochester, NY (US)

( * ) Notice: Subject to any disclaimer, the term of this patent is extended or adjusted under 35 U.S.C. 154(b) by 586 days.

(21) Appl. No.: 12/179,951

(22) Filed: Jul. 25, 2008

(65) Prior Publication Data

US 2009/0118185 A1 May 7, 2009

Related U.S. Application Data

(60) Provisional application No. 60/984,518, filed on Nov. 1, 2007, provisional application No. 60/991,304, filed on Nov. 30, 2007.

(51) Int. Cl.
*A61K 38/37* (2006.01)
*C07K 14/755* (2006.01)

(52) U.S. Cl. ........................................ 530/383; 514/14.1

(58) Field of Classification Search ........................ None
See application file for complete search history.

(56) References Cited

U.S. PATENT DOCUMENTS

| | | | | |
|---|---|---|---|---|
| 5,451,521 | A * | 9/1995 | Kaufman et al. | 435/356 |
| 5,576,291 | A | 11/1996 | Curtis et al. | |
| 5,859,204 | A | 1/1999 | Lollar | |
| 5,880,327 | A | 3/1999 | Lubon et al. | |
| 5,998,589 | A | 12/1999 | Buettner et al. | |
| 6,271,025 | B1 | 8/2001 | Négrier et al. | |
| 6,376,463 | B1 | 4/2002 | Lollar | |
| 6,458,563 | B1 | 10/2002 | Lollar | |
| 6,593,291 | B1 | 7/2003 | Green et al. | |
| 6,599,724 | B1 | 7/2003 | Mikaelsson et al. | |
| 6,759,216 | B1 | 7/2004 | Lollar | |
| 6,770,744 | B2 | 8/2004 | Lollar | |
| 6,780,614 | B2 | 8/2004 | Négrier et al. | |
| 6,800,461 | B2 | 10/2004 | Négrier et al. | |
| 2003/0125232 | A1 | 7/2003 | Griffin et al. | |
| 2003/0166536 | A1 | 9/2003 | Lollar | |
| 2004/0092442 | A1 | 5/2004 | Kaufman et al. | |
| 2004/0147436 | A1 | 7/2004 | Kim et al. | |
| 2004/0197815 | A1 | 10/2004 | Singh et al. | |
| 2007/0265199 | A1 | 11/2007 | Fay et al. | |

OTHER PUBLICATIONS

Sergel, T.A., et al. 2000 Journal of Virology 74(11): 5101-5107.*

Yuan, S-M., et al. 1998 Proteins: Structure, Function, Genetics 30: 136-143.*

Amano et al., "Mutation at either Arg336 or Arg562 in Factor VIII is Insufficient for Complete Resistance to Activated Protein C (APC)—Mediated Inactivation: Implications for the APC Resistance Test," Thromb Haemost 79:557-563 (1998).

Gale et al., "An Engineered Interdomain Disulfide Bond Stabilizes Human Blood Coagulation Factor VIIIa," J Thrombosis and Haemostasis 1(9):1966-1971 (2003) (abstract only).

Hernández (editor), "Factor VIII/von Willebrand Factor Complex in Hemophilia A Treatment: Recent Findings, Emerging Major Role," Journal of Hematology 88(9):1-27 (2003).

Lenting et al., "The Life Cycle of Coagulation Factor VIII in View of Its Structure and Function," Blood 92 (11):3983-3996 (1998).

Lenting et al., "The Sequence of Glu1811-Lys1818 of Human Blood Coagulation Factor VIII Comprises a Binding Site for Activated Factor IX," J Biol Chem 271(4):1935-1940 (1996).

Pipe et al., "Characterization of a Genetically Engineered Inactivation-Resistant Coagulation Factor VIIIa," Proc Natl Acad Sci USA 94:11851-11856 (1997).

Sarafanov et al., "Cell Surface Heparan Sulfate Proteoglycans Participate in Factor VIII Catabolism Mediated by Low Density Lipoprotein Receptor-Related Protein," J Biol Chem 276(15):11970-11979 (2001).

Swaroop et al., "Mutagenesis of a Potential Immunoglobulin-Binding Protein-Binding Site Enhances Secretion of Coagulation Factor VIII," J Biol Chem 272(39):24121-24124 (1997).

Varfaj et al., "Contribution of P4-P3' Residues Surrounding P1 Residues Arg336 and Arg562 in the Activated Protein C-Catalyzed Inactivation of Factor VIIIa," ASH Annual Meeting Blood 108: Abstract 1693 (2006).

Varfaj et al., "P2 and P2' Residues are Important for the Efficient proteolysis of Factor VIIIa at Arg336 Catalyzed by Activated Protein C," ASH Annual Meeting Blood 110: Abstract 2689 (Nov. 16, 2007).

Varfaj et al., "Residues Surrounding Arg336 and Arg562 Contribute to the Disparate Rates of Proteolysis of Factor VIIIa Catalyzed by Activated Protein C," J Biol Chem 282(28):20264-72 (2007).

Varfaj et al., "Role of P1 Residues Arg336 and Arg562 in the Activated-Protein-C-catalysed Inactivation of Factor VIIIa," Biochem. J. 396:355-62 (2006).

Varfaj et al., "The Mutation Leu335Pro in Factor VIII Results in its Rapid Inactivation by Thrombin-catalyzed proteolysis at Arg336," ASH Annual Meeting Blood 110: Abstract 2690 (Nov. 16, 2007).

Wakabayahi et al., "Factor VIII: E113A Represents a High Specific Activity Factor VIII Arising From a Single Point Mutation within the Ca2+ Binding Site," Blood 104(11):479a Abstract 1735 (2004).

Wakabayashi et al., "Residues 110-126 in the A1 Domain of Factor VIII Contain a Ca2+ Binding Site Required for Cofactor Activity," J Biol Chem 279(13):12677-12684 (2004).

Wakabayashi et al., "Residues 110-126 in the Factor VIII Heavy Chain Contain a CA2+ Binding Site Required for Cofactor Activity," Blood 102(11):542a Abstract 1988 (2003).

Wakabayashi et al., "Ca2+ Binding to Both the Heavy and Light Chains of Factor VIII Is Required for Cofactor Activity," Biochem 41:8485-8492 (2002).

Wakabayashi et al., "Identification of Residues Contributing to A2 Domain-Dependent Structural Stability in Factor VIII and Factor VIIIa," J Biol. Chem. 283:11645-11651 (2008).

* cited by examiner

*Primary Examiner* — Marsha Tsay

(74) *Attorney, Agent, or Firm* — LeClairRyan, a Professional Corporation

(57) ABSTRACT

The present invention relates to a recombinant factor VIII that is characterized by one or more mutations within a region surrounding an activated protein C cleavage site, which one or more mutations result in a reduced rate of inactivation by activated protein C. Isolated nucleic acid molecules, recombinant expression vectors, and host cells suitable for expression of the recombinant factor VIII are also disclosed. The recombinant factor VIII can be used for the treatment of clotting disorders, such as hemophilia A.

23 Claims, 5 Drawing Sheets

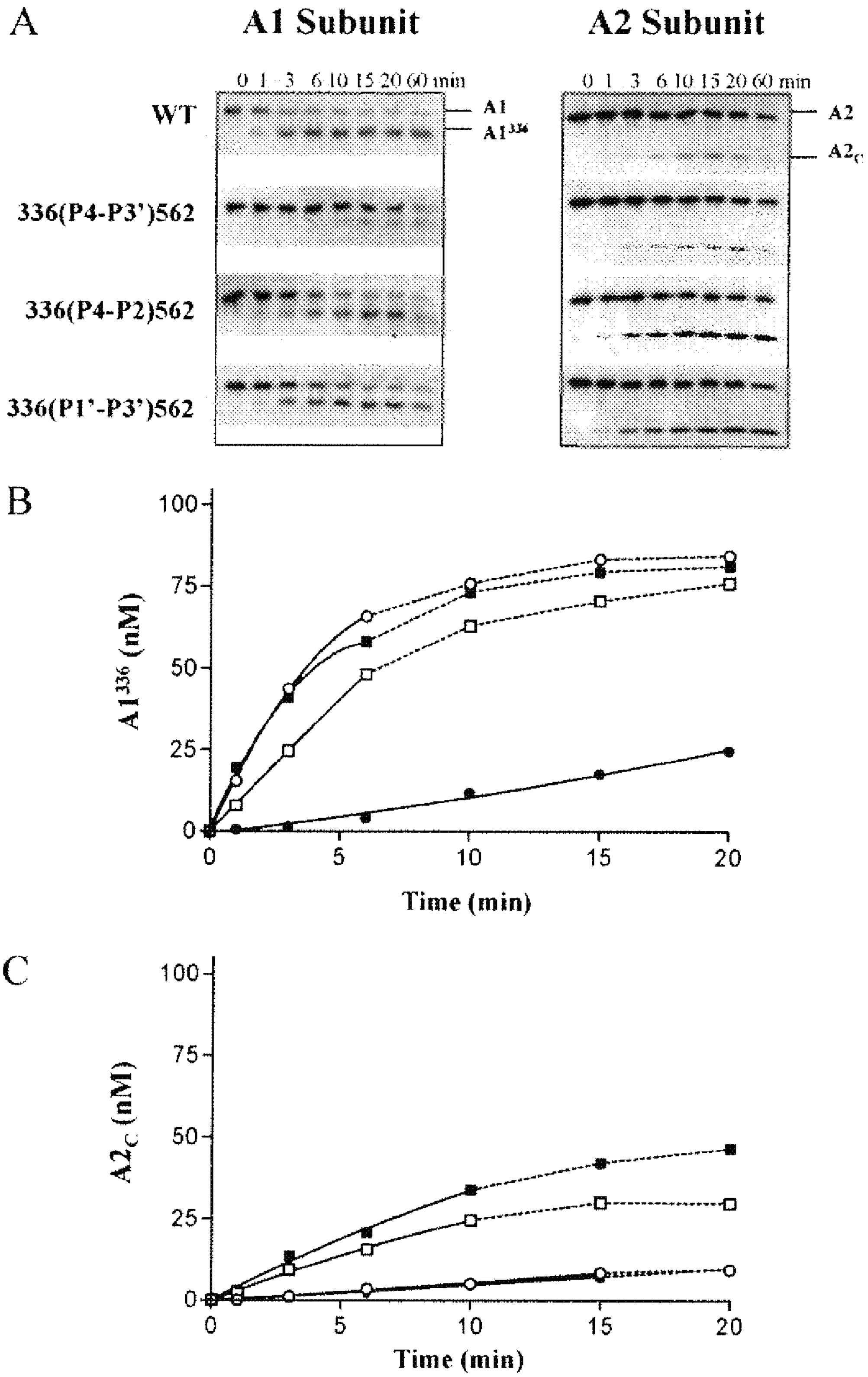
Figures 2A-C

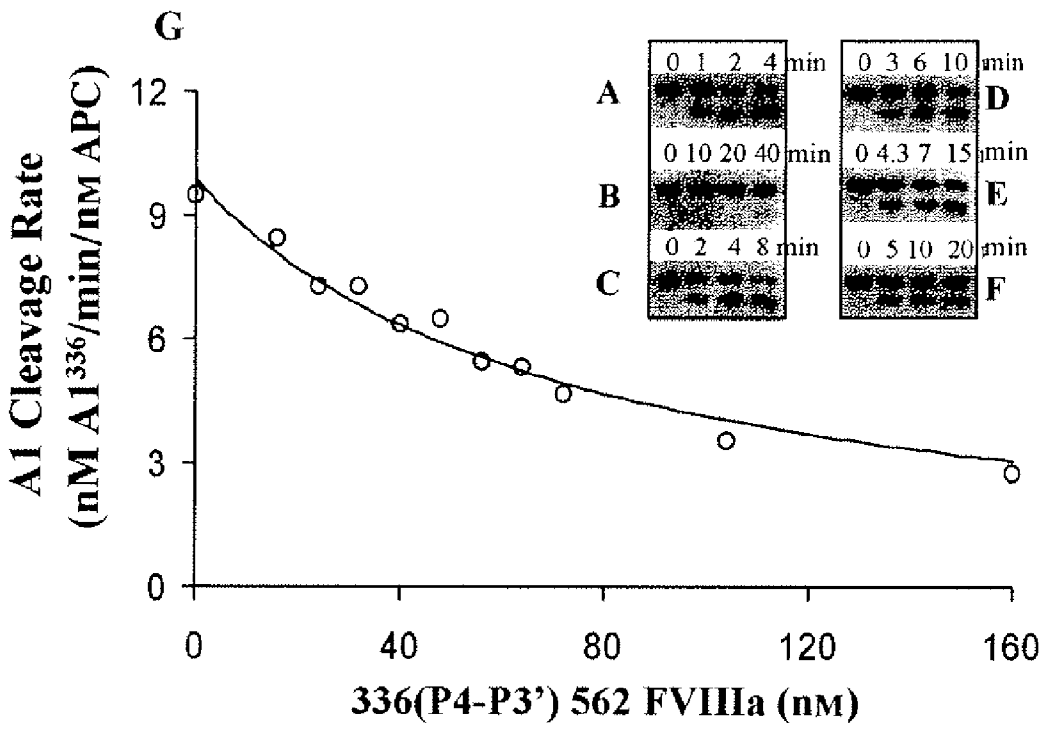
Figures 3A-G

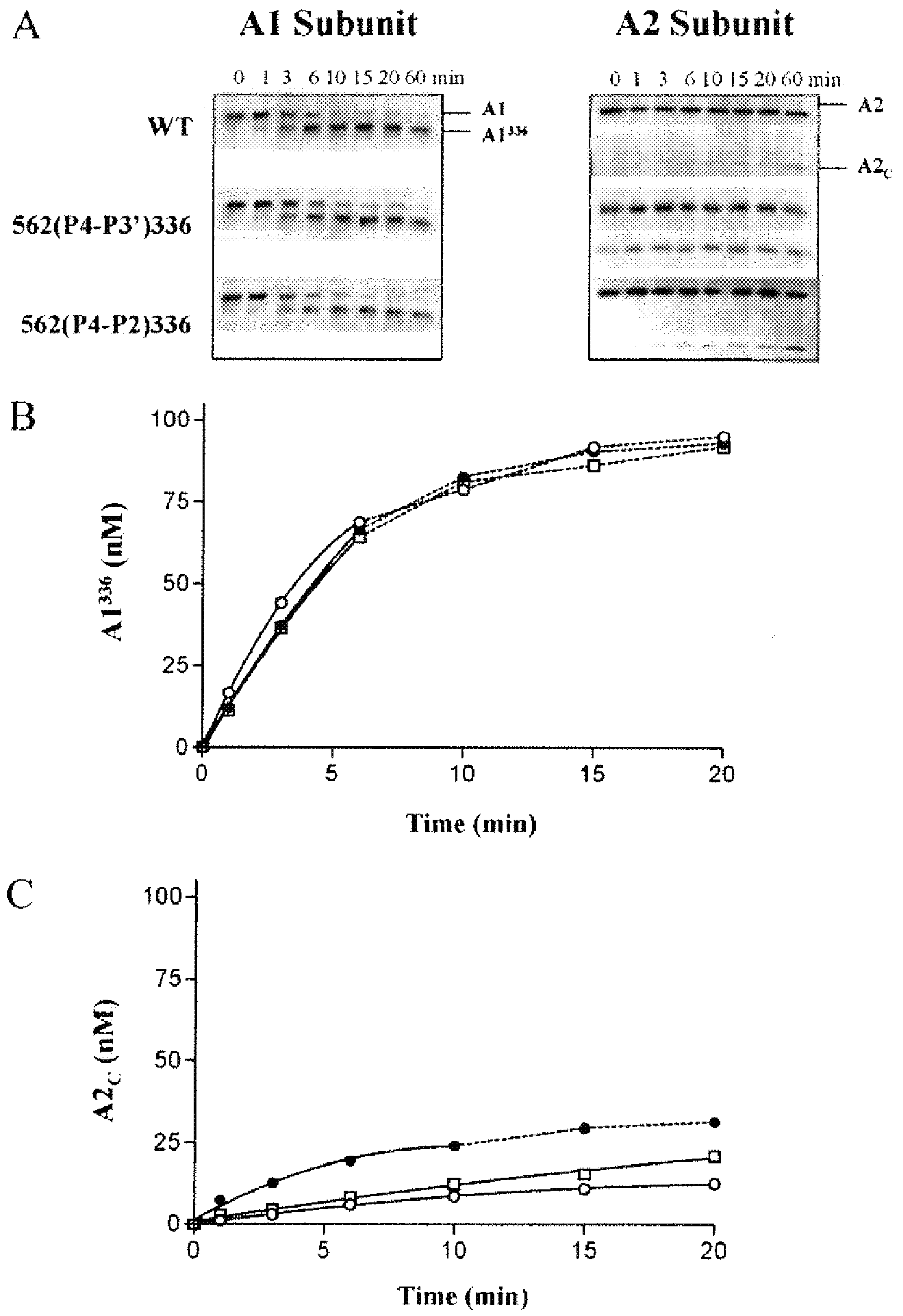
Figures 4A-C

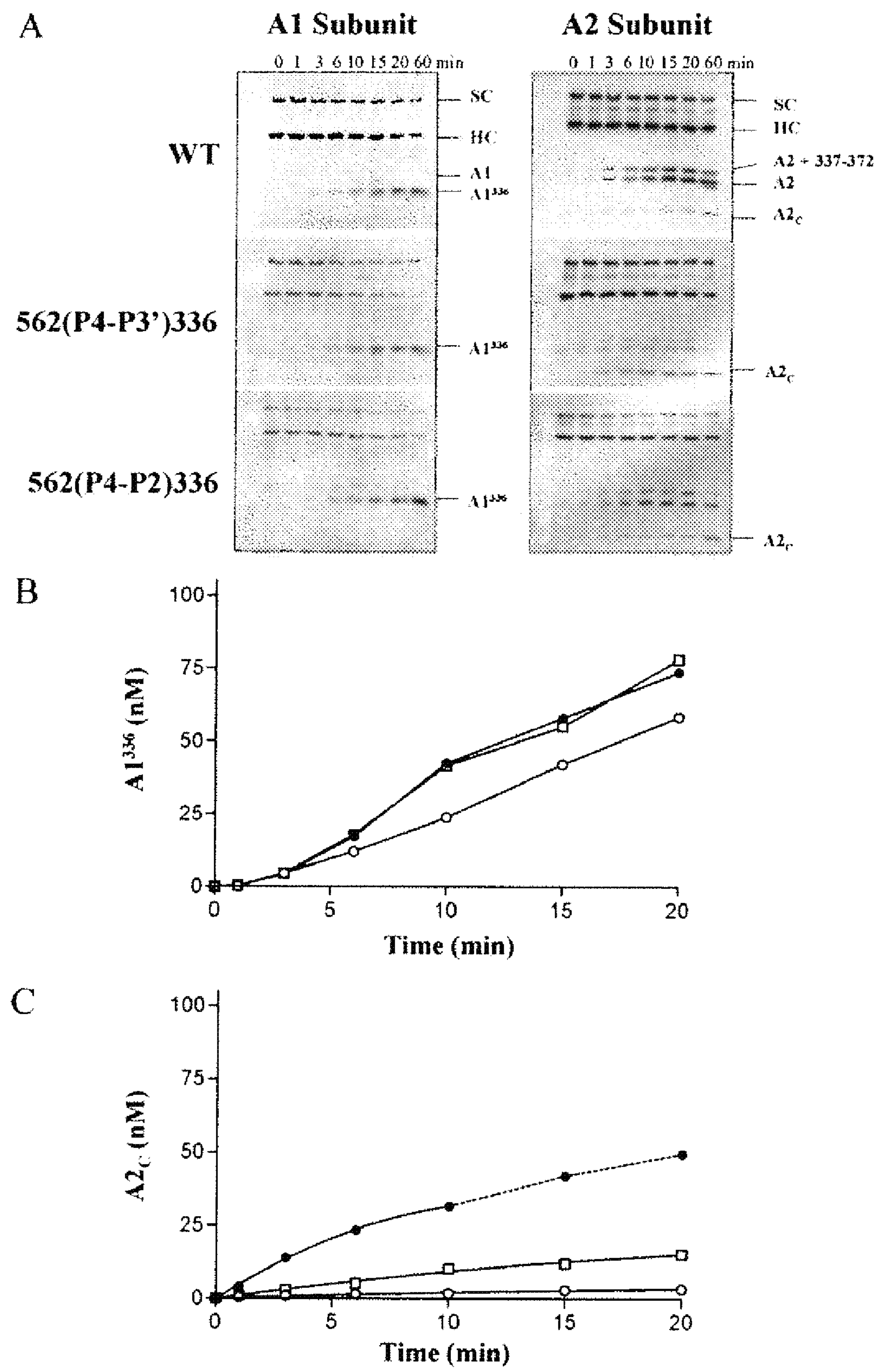
Figures 5A-C

SEQUENCE LISTING

<160> NUMBER OF SEQ ID NOS: 9

<210> SEQ ID NO 1
<211> LENGTH: 6999
<212> TYPE: DNA
<213> ORGANISM: Homo sapiens

<400> SEQUENCE: 1

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact actttttgct     600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca aacactcttg     900
atggaccttg gacagtttct actgttttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca actctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaaagtccg atttatggca tacacagatg aaacctttaa gactcgtgaa    1320
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgct ttctccccaa tccagctgga    1800
gtgcagcttg aggatccaga gttccaagcc tccaacatca tgcacagcat caatggctat    1860
gtttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
```

-continued

```
tcgatggaaa acccaggtct atggattctg ggtgccaca actcagactt tcggaacaga   2100
ggcatgaccg ccttactgaa ggtttctagt tgtgacaaga acactggtga ttattacgag   2160
gacagttatg aagatatttc agcatacttg ctgagtaaaa acaatgccat tgaaccaaga   2220
agcttctccc agaattcaag acaccctagc actaggcaaa agcaatttaa tgccaccaca   2280
attccagaaa atgacataga gaagactgac ccttggtttg cacacagaac acctatgcct   2340
aaaatacaaa atgtctcctc tagtgatttg ttgatgctct tgcgacagag tcctactcca   2400
catgggctat ccttatctga tctccaagaa gccaaatatg agactttttc tgatgatcca   2460
tcacctggag caatagacag taataacagc ctgtctgaaa tgacacactt caggccacag   2520
ctccatcaca gtggggacat ggtatttacc cctgagtcag gcctccaatt aagattaaat   2580
gagaaactgg ggacaactgc agcaacagag ttgaagaaac ttgatttcaa agtttctagt   2640
acatcaaata atctgatttc aacaattcca tcagacaatt tggcagcagg tactgataat   2700
acaagttcct taggaccccc aagtatgcca gttcattatg atagtcaatt agataccact   2760
ctatttggca aaaagtcatc tccccttact gagtctggtg gacctctgag cttgagtgaa   2820
gaaaataatg attcaaagtt gttagaatca ggtttaatga atagccaaga aagttcatgg   2880
ggaaaaaatg tatcgtcaac agagagtggt aggttattta aagggaaaag agctcatgga   2940
cctgctttgt tgactaaaga taatgcctta ttcaaagtta gcatctcttt gttaaagaca   3000
aacaaaactt ccaataattc agcaactaat agaaagactc acattgatgg cccatcatta   3060
ttaattgaga atagtccatc agtctggcaa aatatattag aaagtgacac tgagtttaaa   3120
aaagtgacac ctttgattca tgacagaatg cttatggaca aaaatgctac agctttgagg   3180
ctaaatcata tgtcaaataa aactacttca tcaaaaaaca tggaaatggt ccaacagaaa   3240
aaagagggcc ccattccacc agatgcacaa aatccagata tgtcgttctt taagatgcta   3300
ttcttgccag aatcagcaag gtggatacaa aggactcatg gaaagaactc tctgaactct   3360
gggcaaggcc ccagtccaaa gcaattagta tccttaggac cagaaaaatc tgtggaaggt   3420
cagaatttct tgtctgagaa aaacaaagtg gtagtaggaa agggtgaatt tacaaaggac   3480
gtaggactca aagagatggt tttccaagc agcagaaacc tatttcttac taacttggat   3540
aatttacatg aaaataatac acacaatcaa gaaaaaaaaa ttcaggaaga aatagaaaag   3600
aaggaaacat taatccaaga gaatgtagtt ttgcctcaga tacatacagt gactggcact   3660
aagaatttca tgaagaacct tttcttactg agcactaggc aaaatgtaga aggttcatat   3720
gacggggcat atgctccagt acttcaagat tttaggtcat taaatgattc aacaaataga   3780
acaaagaaac acacagctca tttctcaaaa aaaggggagg aagaaaactt ggaaggcttg   3840
ggaaatcaaa ccaagcaaat tgtagagaaa tatgcatgca ccacaaggat atctcctaat   3900
acaagccagc agaattttgt cacgcaacgt agtaagagag ctttgaaaca attcagactc   3960
ccactagaag aaacagaact tgaaaaaagg ataattgtgg atgacacctc aacccagtgg   4020
tccaaaaaca tgaaacattt gaccccgagc accctcacac agatagacta caatgagaag   4080
gagaaagggg ccattactca gtctccctta tcagattgcc ttacgaggag tcatagcatc   4140
cctcaagcaa atagatctcc attacccatt gcaaaggtat catcatttcc atctattaga   4200
cctatatatc tgaccagggt cctattccaa gacaactctt ctcatcttcc agcagcatct   4260
tatagaaaga aagattctgg ggtccaagaa agcagtcatt tcttacaagg agccaaaaaa   4320
aataaccttt ctttagccat tctaaccttg gagatgactg gtgatcaaag agaggttggc   4380
tccctgggga caagtgccac aaattcagtc acatacaaga aagttgagaa cactgttctc   4440
```

-continued

```
ccgaaaccag acttgcccaa aacatctggc aaagttgaat tgcttccaaa agttcacatt   4500
tatcagaagg acctattccc tacggaaact agcaatgggt ctcctggcca tctggatctc   4560
gtggaaggga gccttcttca gggaacagag ggagcgatta agtggaatga agcaaacaga   4620
cctggaaaag ttccctttct gagagtagca acagaaagct ctgcaaagac tccctccaag   4680
ctattggatc ctcttgcttg ggataaccac tatggtactc agataccaaa agaagagtgg   4740
aaatcccaag agaagtcacc agaaaaaaca gcttttaaga aaaaggatac cattttgtcc   4800
ctgaacgctt gtgaaagcaa tcatgcaata gcagcaataa atgagggaca aaataagccc   4860
gaaatagaag tcacctgggc aaagcaaggt aggactgaaa ggctgtgctc tcaaaaccca   4920
ccagtcttga aacgccatca acgggaaata actcgtacta ctcttcagtc agatcaagag   4980
gaaattgact atgatgatac catatcagtt gaaatgaaga aggaagattt tgacatttat   5040
gatgaggatg aaaatcagag cccccgcagc tttcaaaaga aaacacgaca ctattttatt   5100
gctgcagtgg agaggctctg ggattatggg atgagtagct ccccacatgt tctaagaaac   5160
agggctcaga gtggcagtgt ccctcagttc aagaaagttg ttttccagga atttactgat   5220
ggctccttta ctcagccctt ataccgtgga gaactaaatg aacatttggg actcctgggg   5280
ccatatataa gagcagaagt tgaagataat atcatggtaa ctttcagaaa tcaggcctct   5340
cgtccctatt ccttctattc tagccttatt tcttatgagg aagatcagag gcaaggagca   5400
gaacctagaa aaaactttgt caagcctaat gaaaccaaaa cttacttttg gaaagtgcaa   5460
catcatatgg cacccactaa agatgagttt gactgcaaag cctgggctta tttctctgat   5520
gttgacctgg aaaaagatgt gcactcaggc ctgattggac cccttctggt ctgccacact   5580
aacacactga accctgctca tgggagacaa gtgacagtac aggaatttgc tctgtttttc   5640
accatctttg atgagaccaa aagctggtac ttcactgaaa atatggaaag aaactgcagg   5700
gctccctgca atatccagat ggaagatccc acttttaaag agaattatcg cttccatgca   5760
atcaatggct acataatgga tacactacct ggcttagtaa tggctcagga tcaaaggatt   5820
cgatggtatc tgctcagcat gggcagcaat gaaaacatcc attctattca tttcagtgga   5880
catgtgttca ctgtacgaaa aaaagaggag tataaaatgg cactgtacaa tctctatcca   5940
ggtgtttttg agacagtgga aatgttacca tccaaagctg gaatttggcg ggtggaatgc   6000
cttattggcg agcatctaca tgctgggatg agcacacttt ttctggtgta cagcaataag   6060
tgtcagactc ccctgggaat ggcttctgga cacattagag attttcagat tacagcttca   6120
ggacaatatg gacagtgggc cccaaagctg gccagacttc attattccgg atcaatcaat   6180
gcctggagca ccaaggagcc cttttcttgg atcaaggtgg atctgttggc accaatgatt   6240
attcacggca tcaagaccca gggtgcccgt cagaagttct ccagcctcta catctctcag   6300
tttatcatca tgtatagtct tgatgggaag aagtggcaga cttatcgagg aaattccact   6360
ggaaccttaa tggtcttctt tggcaatgtg gattcatctg ggataaaaca caatattttt   6420
aaccctccaa ttattgctcg atacatccgt ttgcacccaa ctcattatag cattcgcagc   6480
actcttcgca tggagttgat gggctgtgat ttaaatagtt gcagcatgcc attgggaatg   6540
gagagtaaag caatatcaga tgcacagatt actgcttcat cctactttac caatatgttt   6600
gccacctggt ctccttcaaa agctcgactt cacctccaag ggaggagtaa tgcctggaga   6660
cctcaggtga ataatccaaa agagtggctg caagtggact tccagaagac aatgaaagtc   6720
acaggagtaa ctactcaggg agtaaaatct ctgcttacca gcatgtatgt gaaggagttc   6780
ctcatctcca gcagtcaaga tggccatcag tggactctct tttttcagaa tggcaaagta   6840
```

-continued

```
aaggtttttc agggaaatca agactccttc acacctgtgg tgaactctct agacccaccg    6900

ttactgactc gctaccttcg aattcacccc cagagttggg tgcaccagat tgccctgagg    6960

atggaggttc tgggctgcga ggcacaggac ctctactga                           6999
```

<210> SEQ ID NO 2
<211> LENGTH: 2332
<212> TYPE: PRT
<213> ORGANISM: Homo sapiens

<400> SEQUENCE: 2

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350
```

-continued

```
Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780
```

```
Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
            805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr  Asn Lys Thr Ser Asn  Asn Ser Ala
        995                 1000                1005

Thr Asn  Arg Lys Thr His Ile  Asp Gly Pro Ser Leu  Leu Ile Glu
    1010                 1015                 1020

Asn Ser  Pro Ser Val Trp Gln  Asn Ile Leu Glu Ser  Asp Thr Glu
    1025                 1030                 1035

Phe Lys  Lys Val Thr Pro Leu  Ile His Asp Arg Met  Leu Met Asp
    1040                 1045                 1050

Lys Asn  Ala Thr Ala Leu Arg  Leu Asn His Met Ser  Asn Lys Thr
    1055                 1060                 1065

Thr Ser  Ser Lys Asn Met Glu  Met Val Gln Gln Lys  Lys Glu Gly
    1070                 1075                 1080

Pro Ile  Pro Pro Asp Ala Gln  Asn Pro Asp Met Ser  Phe Phe Lys
    1085                 1090                 1095

Met Leu  Phe Leu Pro Glu Ser  Ala Arg Trp Ile Gln  Arg Thr His
    1100                 1105                 1110

Gly Lys  Asn Ser Leu Asn Ser  Gly Gln Gly Pro Ser  Pro Lys Gln
    1115                 1120                 1125

Leu Val  Ser Leu Gly Pro Glu  Lys Ser Val Glu Gly  Gln Asn Phe
    1130                 1135                 1140

Leu Ser  Glu Lys Asn Lys Val  Val Val Gly Lys Gly  Glu Phe Thr
    1145                 1150                 1155

Lys Asp  Val Gly Leu Lys Glu  Met Val Phe Pro Ser  Ser Arg Asn
    1160                 1165                 1170

Leu Phe  Leu Thr Asn Leu Asp  Asn Leu His Glu Asn  Asn Thr His
    1175                 1180                 1185

Asn Gln  Glu Lys Lys Ile Gln  Glu Glu Ile Glu Lys  Lys Glu Thr
```

```
    1190                1195                1200

Leu Ile  Gln Glu Asn Val Val  Leu Pro Gln Ile His  Thr Val Thr
    1205                1210                1215

Gly Thr  Lys Asn Phe Met Lys  Asn Leu Phe Leu Leu  Ser Thr Arg
    1220                1225                1230

Gln Asn  Val Glu Gly Ser Tyr  Glu Gly Ala Tyr Ala  Pro Val Leu
    1235                1240                1245

Gln Asp  Phe Arg Ser Leu Asn  Asp Ser Thr Asn Arg  Thr Lys Lys
    1250                1255                1260

His Thr  Ala His Phe Ser Lys  Lys Gly Glu Glu Glu  Asn Leu Glu
    1265                1270                1275

Gly Leu  Gly Asn Gln Thr Lys  Gln Ile Val Glu Lys  Tyr Ala Cys
    1280                1285                1290

Thr Thr  Arg Ile Ser Pro Asn  Thr Ser Gln Gln Asn  Phe Val Thr
    1295                1300                1305

Gln Arg  Ser Lys Arg Ala Leu  Lys Gln Phe Arg Leu  Pro Leu Glu
    1310                1315                1320

Glu Thr  Glu Leu Glu Lys Arg  Ile Ile Val Asp Asp  Thr Ser Thr
    1325                1330                1335

Gln Trp  Ser Lys Asn Met Lys  His Leu Thr Pro Ser  Thr Leu Thr
    1340                1345                1350

Gln Ile  Asp Tyr Asn Glu Lys  Glu Lys Gly Ala Ile  Thr Gln Ser
    1355                1360                1365

Pro Leu  Ser Asp Cys Leu Thr  Arg Ser His Ser Ile  Pro Gln Ala
    1370                1375                1380

Asn Arg  Ser Pro Leu Pro Ile  Ala Lys Val Ser Ser  Phe Pro Ser
    1385                1390                1395

Ile Arg  Pro Ile Tyr Leu Thr  Arg Val Leu Phe Gln  Asp Asn Ser
    1400                1405                1410

Ser His  Leu Pro Ala Ala Ser  Tyr Arg Lys Lys Asp  Ser Gly Val
    1415                1420                1425

Gln Glu  Ser Ser His Phe Leu  Gln Gly Ala Lys Lys  Asn Asn Leu
    1430                1435                1440

Ser Leu  Ala Ile Leu Thr Leu  Glu Met Thr Gly Asp  Gln Arg Glu
    1445                1450                1455

Val Gly  Ser Leu Gly Thr Ser  Ala Thr Asn Ser Val  Thr Tyr Lys
    1460                1465                1470

Lys Val  Glu Asn Thr Val Leu  Pro Lys Pro Asp Leu  Pro Lys Thr
    1475                1480                1485

Ser Gly  Lys Val Glu Leu Leu  Pro Lys Val His Ile  Tyr Gln Lys
    1490                1495                1500

Asp Leu  Phe Pro Thr Glu Thr  Ser Asn Gly Ser Pro  Gly His Leu
    1505                1510                1515

Asp Leu  Val Glu Gly Ser Leu  Leu Gln Gly Thr Glu  Gly Ala Ile
    1520                1525                1530

Lys Trp  Asn Glu Ala Asn Arg  Pro Gly Lys Val Pro  Phe Leu Arg
    1535                1540                1545

Val Ala  Thr Glu Ser Ser Ala  Lys Thr Pro Ser Lys  Leu Leu Asp
    1550                1555                1560

Pro Leu  Ala Trp Asp Asn His  Tyr Gly Thr Gln Ile  Pro Lys Glu
    1565                1570                1575

Glu Trp  Lys Ser Gln Glu Lys  Ser Pro Glu Lys Thr  Ala Phe Lys
    1580                1585                1590
```

-continued

```
Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995
```

```
Glu Cys  Leu Ile Gly Glu His  Leu His Ala Gly Met  Ser Thr Leu
    2000                 2005                 2010

Phe Leu  Val Tyr Ser Asn Lys  Cys Gln Thr Pro Leu  Gly Met Ala
    2015                 2020                 2025

Ser Gly  His Ile Arg Asp Phe  Gln Ile Thr Ala Ser  Gly Gln Tyr
    2030                 2035                 2040

Gly Gln  Trp Ala Pro Lys Leu  Ala Arg Leu His Tyr  Ser Gly Ser
    2045                 2050                 2055

Ile Asn  Ala Trp Ser Thr Lys  Glu Pro Phe Ser Trp  Ile Lys Val
    2060                 2065                 2070

Asp Leu  Leu Ala Pro Met Ile  Ile His Gly Ile Lys  Thr Gln Gly
    2075                 2080                 2085

Ala Arg  Gln Lys Phe Ser Ser  Leu Tyr Ile Ser Gln  Phe Ile Ile
    2090                 2095                 2100

Met Tyr  Ser Leu Asp Gly Lys  Lys Trp Gln Thr Tyr  Arg Gly Asn
    2105                 2110                 2115

Ser Thr  Gly Thr Leu Met Val  Phe Phe Gly Asn Val  Asp Ser Ser
    2120                 2125                 2130

Gly Ile  Lys His Asn Ile Phe  Asn Pro Pro Ile Ile  Ala Arg Tyr
    2135                 2140                 2145

Ile Arg  Leu His Pro Thr His  Tyr Ser Ile Arg Ser  Thr Leu Arg
    2150                 2155                 2160

Met Glu  Leu Met Gly Cys Asp  Leu Asn Ser Cys Ser  Met Pro Leu
    2165                 2170                 2175

Gly Met  Glu Ser Lys Ala Ile  Ser Asp Ala Gln Ile  Thr Ala Ser
    2180                 2185                 2190

Ser Tyr  Phe Thr Asn Met Phe  Ala Thr Trp Ser Pro  Ser Lys Ala
    2195                 2200                 2205

Arg Leu  His Leu Gln Gly Arg  Ser Asn Ala Trp Arg  Pro Gln Val
    2210                 2215                 2220

Asn Asn  Pro Lys Glu Trp Leu  Gln Val Asp Phe Gln  Lys Thr Met
    2225                 2230                 2235

Lys Val  Thr Gly Val Thr Thr  Gln Gly Val Lys Ser  Leu Leu Thr
    2240                 2245                 2250

Ser Met  Tyr Val Lys Glu Phe  Leu Ile Ser Ser Ser  Gln Asp Gly
    2255                 2260                 2265

His Gln  Trp Thr Leu Phe Phe  Gln Asn Gly Lys Val  Lys Val Phe
    2270                 2275                 2280

Gln Gly  Asn Gln Asp Ser Phe  Thr Pro Val Val Asn  Ser Leu Asp
    2285                 2290                 2295

Pro Pro  Leu Leu Thr Arg Tyr  Leu Arg Ile His Pro  Gln Ser Trp
    2300                 2305                 2310

Val His  Gln Ile Ala Leu Arg  Met Glu Val Leu Gly  Cys Glu Ala
    2315                 2320                 2325

Gln Asp  Leu Tyr
    2330
```

<210> SEQ ID NO 3
<211> LENGTH: 7
<212> TYPE: PRT
<213> ORGANISM: Artificial Sequence
<220> FEATURE:
<223> OTHER INFORMATION: P4-P3' activated protein C cleavage site of A1
      domain, corresponding to wildtype residues 333-339

<400> SEQUENCE: 3

Pro Gln Leu Arg Met Lys Asn
1 5

<210> SEQ ID NO 4
<211> LENGTH: 7
<212> TYPE: PRT
<213> ORGANISM: Artificial Sequence
<220> FEATURE:
<223> OTHER INFORMATION: P4-P3' activated protein C cleavage site of A2 domain, corresponding to wildtype residues 559-565

<400> SEQUENCE: 4

Val Asp Gln Arg Gly Asn Gln
1 5

<210> SEQ ID NO 5
<211> LENGTH: 7
<212> TYPE: PRT
<213> ORGANISM: Artificial Sequence
<220> FEATURE:
<223> OTHER INFORMATION: P4-P3' activated protein C cleavage site of A1 domain, replacement of wildtype residues 333-339

<400> SEQUENCE: 5

Val Asp Gln Arg Gly Asn Gln
1 5

<210> SEQ ID NO 6
<211> LENGTH: 7
<212> TYPE: PRT
<213> ORGANISM: Artificial Sequence
<220> FEATURE:
<223> OTHER INFORMATION: P4-P3' activated protein C cleavage site of A1 domain, replacement of wildtype residues 333-339

<400> SEQUENCE: 6

Val Asp Gln Arg Met Lys Asn
1 5

<210> SEQ ID NO 7
<211> LENGTH: 7
<212> TYPE: PRT
<213> ORGANISM: Artificial Sequence
<220> FEATURE:
<223> OTHER INFORMATION: P4-P3' activated protein C cleavage site of A1 domain, replacement of wildtype residues 333-339

<400> SEQUENCE: 7

Pro Gln Leu Arg Gly Asn Gln
1 5

<210> SEQ ID NO 8
<211> LENGTH: 7
<212> TYPE: PRT
<213> ORGANISM: Artificial Sequence
<220> FEATURE:
<223> OTHER INFORMATION: mutated P4-P3' activated protein C cleavage site of A2 domain, replacement of wildtype residues 559-565

<400> SEQUENCE: 8

Pro Gln Leu Arg Met Lys Asn
1 5

<210> SEQ ID NO 9
<211> LENGTH: 7
<212> TYPE: PRT
<213> ORGANISM: Artificial Sequence
<220> FEATURE:

-continued

```
<223> OTHER INFORMATION: mutated P4-P3' activated protein C cleavage
      site of A2 domain, replacement of wildtype residues 559-565

<400> SEQUENCE: 9

Pro Gln Leu Arg Gly Asn Gln
1               5
```

RECOMBINANT FACTOR VIII HAVING REDUCED INACTIVATION BY ACTIVATED PROTEIN C

This application claims the priority benefit of U.S. Provisional Patent Application Ser. No. 60/984,518, filed Nov. 1, 2007, and U.S. Provisional Patent Application Ser. No. 60/991,304, filed Nov. 30, 2007, each of which is hereby incorporated by reference in its entirety.

This invention was made with government support under grant numbers HL 76213 and HL 38199 awarded by the National Institutes of Health. The government has certain rights in the invention.

BACKGROUND OF THE INVENTION

Hemophilia A, the most common of the severe, inherited bleeding disorders, results from a deficiency or defect in the plasma protein, factor VIII. There is no cure for Hemophilia A and treatment consists of replacement therapy using preparations of the (purified) plasma or recombinant protein.

Factor VIII circulates as an inactive, procofactor form in complex with von Willebrand factor, which stabilizes factor VIII and potentially helps to localize it to sites of vascular injury. Proteolytic activation of factor VIII releases the active cofactor form of the protein, factor VIIIa, facilitating its association in the intrinsic factor Xase complex. This complex, consisting of the serine protease factor IXa and factor VIIIa assembled on an anionic phospholipid membrane surface catalyzes the conversion of factor X to factor Xa, an essential reaction for the propagation phase of blood coagulation. The role of factor VIIIa is to increase the catalytic efficiency of factor IXa by several orders of magnitude (Fay, "Activation of Factor VIII and Mechanisms of Cofactor Action," *Blood Rev.* 18:1-15 (2004)).

Following generation of the fibrin clot, components of the clotting cascade is shut down by a variety of mechanisms. The down regulation of factor Xase occurs by two mechanisms, both of which involve the cofactor, factor VIIIa. One mechanism involves the dissociation of a critical subunit of factor VIIIa, the A2 subunit that exists in a weak affinity interaction with the other subunits of factor VIIIa. The second mechanism occurs by limited proteolysis of factor VIIIa and is catalyzed by the anti-coagulant protease, activated protein C ("APC"). The relative contributions of these two mechanisms to the inactivation of factor VIIIa and subsequent down regulation of factor Xase are not fully understood, although both components are thought to be important in vivo (Fay, "Activation of Factor VIII and Mechanisms of Cofactor Action," *Blood Rev.* 18:1-15 (2004)).

Significant interest exists in stabilizing factor VIIIa activity, since a more "inactivation-resistant" form of the protein would represent a superior therapeutic for hemophilia A, potentially requiring less material to treat the patient (Fay et al., "Mutating Factor VIII: Lessons from Structure to Function," *Blood Reviews* 19:15-27 (2005)). To this end, preparations of factor VIII have been described where mutations have been made in the recombinant protein to prevent the dissociation of the A2 subunit by introducing novel covalent bonds between A2 and other factor VIII domains (Pipe et al., "Characterization of a Genetically Engineered Inactivation-resistant Coagulation Factor VIIIa," *Proc Natl Acad Sci USA* 94:11851-11856 (1997); Gale et al., "An Engineered Interdomain Disulfide Bond Stabilizes Human Blood Coagulation Factor VIIIa," *J. Thrombosis & Haemostasis* 1: 1966-1971 (2003)). In addition, the sites of APC-catalyzed proteolysis (cleavage) in factor VIII are known (Fay, "Activation of Factor VIII and Mechanisms of Cofactor Action," *Blood Rev.* 18:1-15 (2004)) and occur at P1 arginine (Arg) residues at positions 336 and 562. (Residues surrounding the cleavage site are indicated as: $HN_2$-P4-P3-P2-P1-P1'-P2'-P3'-COOH relative to the scissile bond at P1-P1'. This is otherwise known as the P4-P3' region, which extends from residues 333-339 of SEQ ID NO: 2.) Cleavage at each site, i.e., Arg336 and Arg562, contributes to the inactivation of factor VIIIa. Furthermore, cleavage at either site is independent of the other, and the former site appears to be the more reactive site as the rate of cleavage at Arg336 is ~25-fold more rapid than cleavage at Arg562 in factor VIIIa (Varfaj et al., "Role of P1 Residues Arg336 and Arg562 in the Activated-Protein-C-catalysed Inactivation of Factor VIIIa," *Biochem. J.* 396:355-362 (2006)). Thus, attack at Arg336 is the dominant site for APC inactivation of factor VIIIa activity. Prior studies have shown that replacing the P1 Arg residues with other amino acids such as leucine or glutamine by site-directed mutagenesis yield cleavage-resistant forms of factor VIII that are not inactivated by the APC-dependent pathway (Amano et al., "Mutation at either Arg336 or Arg562 in Factor VIII is Insufficient for Complete Resistance to Activated Protein C (APC)-mediated Inactivation: Implications for the APC Resistance Test," *Thrombosis & Haemostasis* 79:557-563 (1998)). This is due to the inability of substrate to correctly dock at the APC active site if the P1 residue is not Arg.

It has since been determined that neither of these types of mutation is desirable in a therapeutic factor VIII, because they substantially eliminate means for down-regulation. This situation could yield a prothrombotic condition, which may cause harm. Thus, a more desirable situation would be to reduce the rate of factor VIIIa inactivation by the APC pathway rather than substantially eliminate this pathway for factor VIIIa inactivation.

The present invention is directed to overcoming these and other deficiencies in the art.

SUMMARY OF THE INVENTION

A first aspect of the present invention relates to a recombinant factor VIII that includes one or more mutations within a region surrounding an activated protein C cleavage site, which one or more mutations result in a reduced rate of inactivation by activated protein C.

A second aspect of the present invention relates to a pharmaceutical composition that includes the recombinant factor VIII according to the first aspect of the present invention.

A third aspect of the present invention relates to an isolated nucleic acid molecule encoding a recombinant factor VIII according to the first aspect of the present invention. Also included within this aspect of the present invention are recombinant DNA expression systems that contain a DNA molecule encoding the recombinant factor VIII of the present invention, and recombinant host cells that contain a DNA molecule and/or recombinant expression system of the present invention.

A fourth aspect of the present invention relates to a method of making a recombinant factor VIII that includes: growing a host cell according to the third aspect of the present invention under conditions whereby the host cell expresses the recombinant factor VIII; and isolating the recombinant factor VIII.

A fifth aspect of the present invention relates to a method of treating an animal for hemophilia A. This method includes: administering to an animal exhibiting hemophilia A an effective amount of the recombinant factor VIII according to the first aspect of the present invention, whereby the animal exhibits effective blood clotting following vascular injury.

BRIEF DESCRIPTION OF THE DRAWINGS

FIGS. 2A-C show cleavage of A1 and A2 subunits of 336 (P4-P3')562 factor VIIIa mutants by APC. WT (○), 336(P4-P3')562 (●), 336(P4-P2)562 (□), and 336(P1'-P3')562 (■) factor VIII forms (130 nM) were activated by thrombin (10 nM) and then reacted with APC (2 nM in WT reaction and 40 nM in mutant reactions). Aliquots were taken at various time points (0-60 min) and subjected to SDS-PAGE. A1 (and $A1^{336}$) and A2 (and $A2_C$) subunits were visualized by Western blotting using 58.12 (anti-A1) and R8B12 (anti-A2) monoclonal antibodies (FIG. 2A). Product concentrations were calculated based on the density values and plotted as a function of time (FIGS. 2B-C). Continuous lines were drawn from the curve fitting as described in the Examples.

FIGS. 3A-G show the effect of the 336(P4-P3')562 mutant on A1 subunit cleavage of WT factor VIIIa by APC. WT factor VIII (130 nM) in the presence of 336(P4-P3')562 mutant (0-200 nM) was activated by thrombin (20 nM) and then reacted with APC (2 nM). Aliquots were taken at various time points (0-20 min) and subjected to SDS-PAGE. The A1 subunit and $A1^{336}$ fragment were visualized by Western blot analysis using 58.12 (anti-A1) monoclonal antibody and their concentrations were calculated based on the scanned density values. The A1 band (upper band of each blot) represents the A1 subunit of uncleaved WT and 336(P4-P3')562 mutant, whereas the $A1^{336}$ band (lower band of each blot) represents the product fragment of the WT A1 subunit. FIGS. 3A-F show the Western blot results for the A1 subunit cleavage of: WT (130 nM) (FIG. 3A); 336(P4-P3')562 mutant (130 nM) (FIG. 3B); and WT (130 nM) in the presence of 40, 90, 130 and 200 nM 336(P4-P3')562 factor VIII mutant, respectively (FIGS. 3C-F). The amount of the $A1^{336}$ (nM) generated over time was determined based on the amount of WT A1 substrate, calculated by subtracting the amount of the mutant A1 from the total amount of A1 subunit. The initial velocity of A1 cleavage was estimated and plotted as a function of 336(P4-P3')562 mutant concentration and continuous lines were drawn from the curve fitting as described in the Examples (FIG. 3G).

FIGS. 4A-C show the cleavage of A1 and A2 subunits of 562(P4-P3')336 factor VIIIa mutants by APC. WT (○), 562 (P4-P3')336 (●), and 562(P4-P2)336 (□) factor VIII forms (130 nM) were activated by thrombin (10 nM), then reacted by APC (2 nM) as described in the legend to FIGS. 2A-C. Aliquots were taken at various time points (0-60 min) and subjected to SDS-PAGE. A1 (and $A1^{336}$) and A2 (and $A2_C$) subunits were visualized by Western blotting using 58.12 (anti-A1) and R8B12 (anti-A2) monoclonal antibodies (FIG. 4A) and their concentrations were calculated based on the density values and plotted as a function of time (FIGS. 4B-C). Continuous lines were drawn from the curve fitting as described in the Examples.

FIGS. 5A-C show the cleavage of A1 and A2 subunits of 562(P4-P3')336 factor VIII mutants by APC. WT (○), 562 (P4-P3')336 (●), and 562(P4-P2)336 (□) factor VIII forms (130 nM) were reacted by APC (2 nM). Aliquots were taken at various time points (0-60 min) and subjected to SDS-PAGE. Factor VIII single chain and heavy chain, A1 (and $A1^{336}$) and A2 (and $A2_C$) subunits were visualized by Western blotting using 58.12 (anti-A1) and R8B12 (anti-A2) monoclonal antibodies (FIG. 5A). Product concentrations were calculated based on the density values and plotted as a function of time (FIGS. 5B-C). Continuous lines in FIG. 5C were drawn from the curve fitting as described in the Examples.

DETAILED DESCRIPTION OF THE INVENTION

Figure 1:
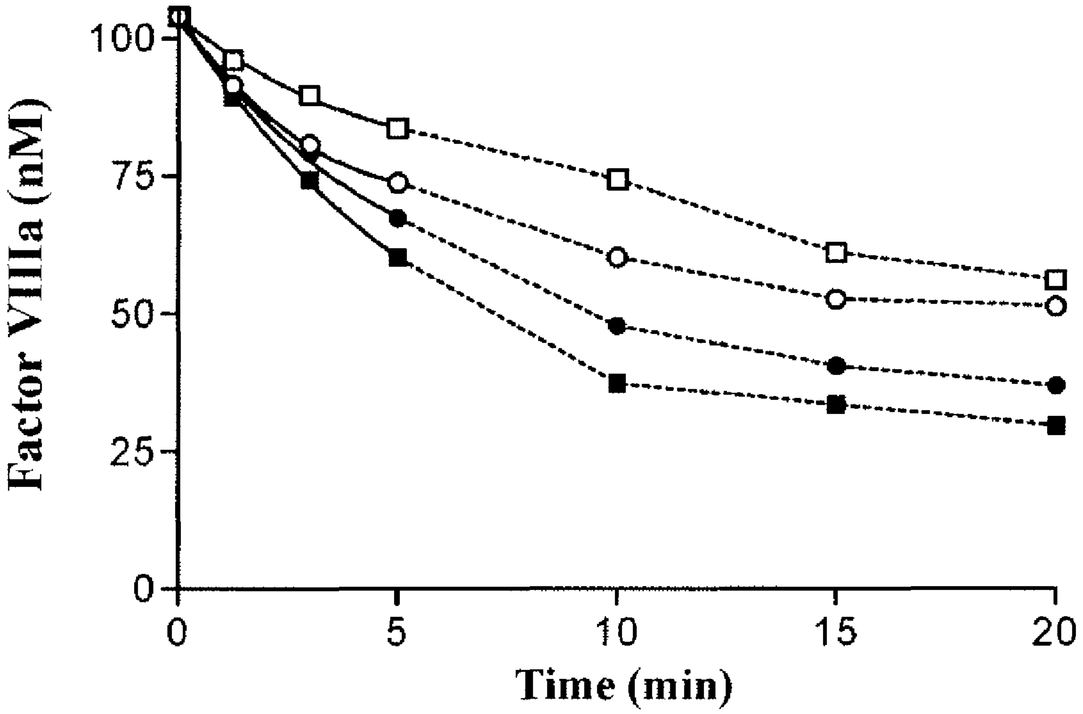
FIG. 1 shows the inactivation of recombinant 336(P4-P3') 562 factor VIIIa mutants by APC. WT (○), 336(P4-P3')562 (●), 336(P4-P2)562 (□), and 336(P1'-P3')562 (■) factor VIII forms (130 nM) were activated by thrombin (10 nM). Factor VIIIa inactivation was then monitored over time in the presence of APC (2 nM in WT reaction and 40 nM in mutant reactions) using a factor Xa generation assay. APC-catalyzed inactivation values were corrected by subtracting the corresponding values for factor VIIIa decay observed in the absence of APC and continuous lines were drawn through initial time points from the curve fitting as described in the Examples.

The present invention relates to a recombinant factor VIII having one or more mutations within a region surrounding an activated protein C cleavage site, which one or more mutations result in a reduced rate of inactivation by activated protein C.

The recombinant factor VIII of the present invention can be prepared by modifying the amino acid sequence of a wild-type factor VIII or a mutant factor VIII that has otherwise been modified to affect other properties of the factor VIII, such as antigenicity, circulating half-life, protein secretion, affinity for factor IXa and/or factor X, altered factor VIII-inactivation cleavage sites, stability of the activated factor VIIIa form, immunogenicity, shelf-life, etc.

Suitable wild-type factor VIII that can be modified in accordance with the present invention can be from various animals including, without limitation, mammals such as humans (see, e.g., GenBank Accession Nos. AAA52484 (amino acid) and K01740 (nucleotide); and GenBank Accession Nos. CAD97566 (amino acid) and AX746360 (nucleotide), which are hereby incorporated by reference in their entirety), rats (see, e.g., GenBank Accession Nos. AAQ21580 (amino acid) and AY362193 (nucleotide), which are hereby incorporated by reference in their entirety), mice (see, e.g., GenBank Accession Nos. AAA37385 (amino acid) and L05573 (nucleotide), which are hereby incorporated by reference in their entirety), guinea pigs, dogs (see, e.g., GenBank Accession Nos. AAB87412 (amino acid) and AF016234 (nucleotide); and GenBank Accession Nos. AAC05384 (amino acid) and AF049489 (nucleotide), which are hereby incorporated by reference in their entirety), cats, monkeys, chimpanzees (see, e.g., GenBank Accession Nos. XP_529212 (amino acid) and XM_529212 (nucleotide), which are hereby incorporated by reference in their entirety), orangutans, cows, horses, sheep, pigs (see, e.g., GenBank Accession Nos. NP_999332 (amino acid) and NM_214167 (nucleotide), which are hereby incorporated by reference in their entirety), goats, rabbits, and chickens. These and other sequences are also available electronically via the Haemophilia A Mutation, Structure, Test and Resource Site (or HAMSTeRS), which further provides an alignment of human, porcine, murine, and canine factor VIII proteins. Thus, the conservation and homology among mammalian factor VIII proteins is well known.

By way of example, the human factor VIII cDNA nucleotide and predicted amino acid sequences are shown below in SEQ ID NOs: 1 and 2, respectively. Human factor VIII is synthesized as an approximately 300 kDa single chain protein with internal sequence homology that defines the "domain"

sequence $NH_2$-A1-A2-B-A3-C1-C2-COOH. In a factor VIII molecule, a "domain," as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO: 2):

A1, residues $Ala_1$-$Arg_{372}$;
A2, residues $Ser_{373}$-$Arg_{740}$;
B, residues $Ser_{741}$-$Arg_{1648}$;
A3, residues $Ser_{1690}$-$Ile_{2032}$;
C1, residues $Arg_{2033}$-$Asn_{2172}$; and
C2, residues $Ser_{2173}$-$Tyr_{2332}$.

The A3-C1-C2 sequence includes residues $Ser_{1690}$-$Tyr_{2332}$. The remaining sequence, residues $Glu_{1649}$-$Arg_{1689}$, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

The gene encoding the wild-type human factor VIII has a nucleotide sequence of SEQ ID NO: 1, as follows:

```
gccaccagaagatactacctgggtgcagtggaactgtcatgggactatat
gcaaagtgatctcggtgagctgcctgtggacgcaagatttcctcctagag
tgccaaaatcttttccattcaacacctcagtcgtgtacaaaaagactctg
tttgtagaattcacggatcaccttttcaacatcgctaagccaaggccacc
ctggatgggtctgctaggtcctaccatccaggctgaggtttatgatacag
tggtcattacacttaagaacatggcttcccatcctgtcagtcttcatgct
gttggtgtatcctactggaaagcttctgagggagctgaatatgatgatca
gaccagtcaaagggagaaagaagatgataaagtcttccctggtggaagcc
atacatatgtctggcaggtcctgaaagagaatggtccaatggcctctgac
ccactgtgccttacctactcatatctttctcatgtggacctggtaaaaga
cttgaattcaggcctcattggagccctactagtatgtagagaagggagtc
tggccaaggaaaagacacagaccttgcacaaatttatactacttttgct
gtatttgatgaagggaaaagttggcactcagaaacaaagaactccttgat
gcaggatagggatgctgcatctgctcgggcctggcctaaaatgcacacag
tcaatggttatgtaaacaggtctctgccaggtctgattggatgccacagg
aaatcagtctattggcatgtgattggaatgggcaccactcctgaagtgca
ctcaatattcctcgaaggtcacacatttcttgtgaggaaccatcgccagg
cgtccttggaaatctcgccaataactttccttactgctcaaacactcttg
atggaccttggacagtttctactgttttgtcatatctcttcccaccaaca
tgatggcatggaagcttatgtcaaagtagacagctgtccagaggaacccc
aactacgaatgaaaaataatgaagaagcggaagactatgatgatgatctt
actgattctgaaatggatgtggtcaggtttgatgatgacaactctccttc
```

-continued

```
ctttatccaaattcgctcagttgccaagaagcatcctaaaacttgggtac
attacattgctgctgaagaggaggactgggactatgctcccttagtcctc
gcccccgatgacagaagttataaaagtcaatatttgaacaatggccctca
gcggattggtaggaagtacaaaaaagtccgatttatggcatacacagatg
aaacctttaagactcgtgaagctattcagcatgaatcaggaatcttggga
cctttactttatggggaagttggagacacactgttgattatatttaagaa
tcaagcaagcagaccatataacatctaccctcacggaatcactgatgtcc
gtcctttgtattcaaggagattaccaaaaggtgtaaaacatttgaaggat
tttccaattctgccaggagaaatattcaaatataaatggacagtgactgt
agaagatgggccaactaaatcagatcctcggtgcctgacccgctattact
ctagtttcgttaatatggagagagatctagcttcaggactcattggccct
ctcctcatctgctacaaagaatctgtagatcaaagaggaaaccagataat
gtcagacaagaggaatgtcatcctgttttctgtatttgatgagaaccgaa
gctggtacctcacagagaatatacaacgctttctccccaatccagctgga
gtgcagcttgaggatccagagttccaagcctccaacatcatgcacagcat
caatggctatgtttttgatagtttgcagttgtcagtttgtttgcatgagg
tggcatactggtacattctaagcattggagcacagactgacttcctttct
gtcttcttctctggatataccttcaaacacaaaatggtctatgaagacac
actcaccctattcccattctcaggagaaactgtcttcatgtcgatggaaa
acccaggtctatggattctggggtgccacaactcagactttcggaacaga
ggcatgaccgccttactgaaggtttctagttgtgacaagaacactggtga
ttattacgaggacagttatgaagatatttcagcatacttgctgagtaaaa
acaatgccattgaaccaagaagcttctcccagaattcaagacaccctagc
actaggcaaaagcaatttaatgccaccacaattccagaaaatgacataga
gaagactgacccttggtttgcacacagaacacctatgcctaaaatacaaa
atgtctcctctagtgatttgttgatgctcttgcgacagagtcctactcca
catgggctatccttatctgatctccaagaagccaaatatgagactttttc
tgatgatccatcacctggagcaatagacagtaataacagcctgtctgaaa
tgacacacttcaggccacagctccatcacagtggggacatggtatttacc
cctgagtcaggcctccaattaagattaaatgagaaactggggacaactgc
agcaacagagttgaagaaacttgatttcaaagtttctagtacatcaaata
atctgatttcaacaattccatcagacaatttggcagcaggtactgataat
acaagttccttaggacccccaagtatgccagttcattatgatagtcaatt
agataccactctatttggcaaaaagtcatctccccttactgagtctggtg
gacctctgagcttgagtgaagaaaataatgattcaaagttgttagaatca
ggtttaatgaatagccaagaaagttcatggggaaaaaatgtatcgtcaac
agagagtggtaggttatttaaagggaaaagagctcatggacctgctttgt
tgactaaagataatgccttattcaaagttagcatctctttgttaaagaca
aacaaaacttccaataattcagcaactaatagaaagactcacattgatgg
cccatcattattaattgagaatagtccatcagtctggcaaaatatattag
```

-continued

```
aaagtgacactgagtttaaaaaagtgacacctttgattcatgacagaatg
cttatggacaaaaatgctacagctttgaggctaaatcatatgtcaaataa
aactacttcatcaaaaaacatggaaatggtccaacagaaaaaagagggcc
ccattccaccagatgcacaaaatccagatatgtcgttctttaagatgcta
ttcttgccagaatcagcaaggtggatacaaaggactcatggaaagaactc
tctgaactctgggcaaggccccagtccaaagcaattagtatccttaggac
cagaaaaatctgtggaaggtcagaatttcttgtctgagaaaaacaaagtg
gtagtaggaaagggtgaatttacaaaggacgtaggactcaaagagatggt
tttccaagcagcagaaacctatttcttactaacttggataatttacatg
aaaataatacacacaatcaagaaaaaaaaattcaggaagaaatagaaaag
aaggaaacattaatccaagagaatgtagttttgcctcagatacatacagt
gactggcactaagaatttcatgaagaaccttttcttactgagcactaggc
aaaatgtagaaggttcatatgacggggcatatgctccagtacttcaagat
tttaggtcattaaatgattcaacaaatagaacaaagaaacacacagctca
tttctcaaaaaaaggggaggaagaaaacttggaaggcttgggaaatcaaa
ccaagcaaattgtagagaaatatgcatgcaccacaaggatatctcctaat
acaagccagcagaattttgtcacgcaacgtagtaagagagctttgaaaca
attcagactcccactagaagaaacagaacttgaaaaaaggataattgtgg
atgacacctcaacccagtggtccaaaaacatgaaacatttgaccccgagc
accctcacacagatagactacaatgagaaggagaaaggggccattactca
gtctcccttatcagattgccttacgaggagtcatagcatccctcaagcaa
atagatctccattacccattgcaaaggtatcatcatttccatctattaga
cctatatatctgaccagggtcctattccaagacaactcttctcatcttcc
agcagcatcttatagaaagaaagattctggggtccaagaaagcagtcatt
tcttacaaggagccaaaaaaaaataacctttctttagccattctaaccttg
gagatgactggtgatcaaagagaggttggctccctggggacaagtgccac
aaattcagtcacatacaagaaagttgagaacactgttctcccgaaaccag
acttgcccaaaacatctggcaaagttgaattgcttccaaaagttcacatt
tatcagaaggacctattccctacggaaactagcaatgggtctcctggcca
tctggatctcgtggaagggagccttcttcagggaacagagggagcgatta
agtggaatgaagcaaacagacctggaaaagttccctttctgagagtagca
acagaaagctctgcaaagactccctccaagctattggatcctcttgcttg
ggataaccactatggtactcagataccaaaagaagagtggaaatcccaag
agaagtcaccagaaaaaacagcttttaagaaaaaggataccattttgtcc
ctgaacgcttgtgaaagcaatcatgcaatagcagcaataaatgagggaca
aaataagcccgaaatagaagtcacctgggcaaagcaaggtaggactgaaa
ggctgtgctctcaaaacccaccagtcttgaaacgccatcaacgggaaata
actcgtactactcttcagtcagatcaagaggaaattgactatgatgatac
catatcagttgaaatgaagaaggaagattttgacatttatgatgaggatg
aaaatcagagccccccgcagctttcaaaagaaaacacgacactattttatt
```

-continued

```
gctgcagtggagaggctctgggattatgggatgagtagctccccacatgt
tctaagaaacagggctcagagtggcagtgtccctcagttcaagaaagttg
ttttccaggaatttactgatggctcctttactcagcccttataccgtgga
gaactaaatgaacatttgggactcctggggccatatataagagcagaagt
tgaagataatatcatggtaactttcagaaatcaggcctctcgtccctatt
ccttctattctagccttatttcttatgaggaagatcagaggcaaggagca
gaacctagaaaaaactttgtcaagcctaatgaaaccaaaacttacttttg
gaaagtgcaacatcatatggcacccactaaagatgagtttgactgcaaag
cctgggcttatttctctgatgttgacctggaaaaagatgtgcactcaggc
ctgattggaccccttctggtctgccacactaacacactgaaccctgctca
tgggagacaagtgacagtacaggaatttgctctgtttttcaccatctttg
atgagaccaaaagctggtacttcactgaaaatatggaaagaaactgcagg
gctccctgcaatatccagatggaagatcccacttttaaagagaattatcg
cttccatgcaatcaatggctacataatggatacactacctggcttagtaa
tggctcaggatcaaaggattcgatggtatctgctcagcatgggcagcaat
gaaaacatccattctattcatttcagtggacatgtgttcactgtacgaaa
aaaagaggagtataaaatggcactgtacaatctctatccaggtgtttttg
agacagtggaaatgttaccatccaaagctggaatttggcgggtggaatgc
cttattggcgagcatctacatgctgggatgagcacactttttctggtgta
cagcaataagtgtcagactccccctgggaatggcttctggacacattagag
attttcagattacagcttcaggacaatatggacagtgggccccaaagctg
gccagacttcattattccggatcaatcaatgcctggagcaccaaggagcc
cttttcttggatcaaggtggatctgttggcaccaatgattattcacggca
tcaagacccagggtgcccgtcagaagttctccagcctctacatctctcag
tttatcatcatgtatagtcttgatgggaagaagtggcagacttatcgagg
aaattccactggaaccttaatggtcttctttggcaatgtggattcatctg
ggataaaacacaatatttttaaccctccaattattgctcgatacatccgt
ttgcacccaactcattatagcattcgcagcactcttcgcatggagttgat
gggctgtgatttaaatagttgcagcatgccattgggaatggagagtaaag
caatatcagatgcacagattactgcttcatcctactttaccaatatgttt
gccacctggtctccttcaaaagctcgacttcacctccaagggaggagtaa
tgcctggagacctcaggtgaataatccaaaagagtggctgcaagtggact
tccagaagacaatgaaagtcacaggagtaactactcagggagtaaaatct
ctgcttaccagcatgtatgtgaaggagttcctcatctccagcagtcaaga
tggccatcagtggactctcttttttcagaatggcaaagtaaaggtttttc
agggaaatcaagactccttcacacctgtggtgaactctctagacccaccg
ttactgactcgctaccttcgaattcacccccagagttgggtgcaccagat
tgccctgaggatggaggttctgggctgcgaggcacaggacctctactga
```

The wild-type human factor VIII encoded by SEQ ID NO: 1 has an amino acid sequence of SEQ ID NO:2, as follows:

ATRRYYLGAVELSWDYMQSDLGELPVDARFPPRVPKSFPFNTSVVYKKTL
FVEFTVHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLFCHISSHQHDGMEAYVKVDSCPEEPQLRMKNNEEAEDYDDDL
TDSEMDVVRFDDDNSPSFIQIRSVAKKHPKTWVHYIAAEEEDWDYAPLVL
APDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNR
GMTALLKVSSCDKNTGDYYEDSYEDISAYLLSKNNAIEPRSFSQNSRHPS
TRQKQFNATTIPENDIEKTDPWFAHRTPMPKIQNVSSSDLLMLLRQSPTP
HGLSLSDLQEAKYETFSDDPSEGAIDSNNSLSEMTHFRPQLHHSGDMVFT
PESGLQLRLNEKLGTTAATELKKLDFKVSSTSNNLISTIPSDNLAAGTDN
TSSLGPPSMPVHYDSQLDTTLFGKKSSPLTESGGPLSLSEENNDSKLLES
GLMNSQESSWGKNVSSTESGRLFKGKRAHGPALLTKDNALFKVSISLLKT
NKTSNNSATNRKTHIDGPSLLIENSPSVWQNILESDTEFKKVTPLIHDRM
LMDKNATALRLNHMSNKTTSSKNMEMVQQKKEGPIPPDAQNPDMSFFKML
FLPESARWIQRTHGKNSLNSGQGPSPKQLVSLGPEKSVEGQNFLSEKNKV
VVGKGEFTKDVGLKEMVFPSSRNLFLTNLDNLHENNTHNQEKKIQEEIEK
KETLIQENVVLPQIHTVTGTKNFMKNLFLLSTRQNVEGSYEGAYAPVLQD
FRSLNDSTNRTKKHTAHFSKKGEEENLEGLGNQTKQIVEKYACTTRISPN
TSQQNFVTQRSKRALKQFRLPLEETELEKRIIVDDTSTQWSKNMKHLTPS
TLTQIDYNEKEKGAITQSPLSDCLTRSHSIPQANRSPLPIAKVSSFPSIR
PIYLTRVLFQDNSSHLPAASYRKKDSGVQESSHFLQGAKKNNLSLAILTL
EMTGDQREVGSLGTSATNSVTYKKVENTVLPKPDLPKTSGKVELLPKVHI
YQKDLFPTETSNGSPGHLDLVEGSLLQGTEGAIKWNEANRPGKVPFLRVA
TESSAKTPSKLLDPLAWDNHYGTQIPKEEWKSQEKSPEKTAFKKKDTILS
LNACESNHAIAAINEGQNKPEIEVTWAKQGRTERLCSQNPPVLKRHQREI
TRTTLQSDQEEIDYDDTISVEMKKEDFDIYDEDENQSPRSFQKKTRHYFI
AAVERLWDYGMSSSPHVLRNRAQSGSVPQFKKVVFQEFTDGSFTQPLYRG
ELNEHLGLLGPYIRAEVEDNIMVTFRNQASRPYSFYSSLISYEEDQRQGA
EPRKNFVKPNETKTYFWKVQHHMAPTKDEFDCKAWAYFSDVDLEKDVHSG
LIGPLLVCHTNTLNPAHGRQVTVQEFALFFTIFDETKSWYFTENMERNCR
APCNIQMEDPTFKENYRFHAINGYIMDTLPGLVMAQDQRIRWYLLSMGSN
ENIHSIHFSGHVFTVRKKEEYKMALYNLYPGVFETVEMLPSKAGIWRVEC
LIGEHLHAGMSTLFLVYSNKCQTPLGMASGHIRDFQITASGQYGQWAPKL

-continued

ARLHYSGSINAWSTKEPFSWIKVDLLAPMIIHGIKTQGARQKFSSLYISQ
FIIMYSLDGKKWQTYRGNSTGTLMVFFGNVDSSGIKHNIFNPPIIARYIR
LHPTHYSIRSTLRMELMGCDLNSCSMPLGMESKAISDAQITASSYFTNMF
ATWSPSKARLHLQGRSNAWRPQVNNPKEWLQVDFQKTMKVTGVTTQGVKS
LLTSMYVKEFLISSSQDGHQWTLFFQNGKVKVFQGNQDSFTPVVNSLDPP
LLTRYLRIHPQSWVHQIALRMEVLGCEAQDLY

In SEQ ID NO: 2, the P4-P3' regions surrounding Arg336 and Arg562 are underlined, and the P1 Arg residue is shown in bold typeface.

The recombinant factor VIII of the present invention includes a substitution of one or more amino acid residues within a region surrounding an activated protein C cleavage site, except that the cleavable Arg scissile bond is not substituted. The region surrounding the activated protein C cleavage site is preferably within about 10 amino acids on either side of the Arg scissile bond, more preferably about 5 amino acids on either side of the Arg scissile bond. Thus, for substitutions in the region surrounding the Arg336 residue, the one or more substitutions is preferably within the range of residues 326-335 and/or 337-346 of the wildtype sequence, more preferably residues 331-335 and/or 337-341, most preferably 333-335 and/or 337-339; and for substitutions in the region surrounding the Arg562 residue, the one or more substitutions is preferably within the range of residues 552-561 and/or 563-572 of the wildtype sequence, more preferably residues 557-561 and/or 563-567, most preferably 559-561 and/or 563-565. In the most preferred embodiments, the one or more substitutions appears within the P4-P3' activated protein C cleavage site, which can be the site corresponding to wildtype residues 333-339 (PQLRMKN, SEQ ID NO: 3) of the A1 domain or the site corresponding to residues 559-565 (VDQRGNQ, SEQ ID NO: 4) of the A2 domain.

According to one embodiment, the recombinant factor VIII includes a substitution of two or more residues within SEQ ID NO: 3 (i.e., aa 333-339 of SEQ ID NO: 2) except for Arg336. Exemplary mutant P4-P3' regions, which include the substitution of two or more amino acids within SEQ ID NO: 3 include, without limitation, VDQRGNQ (SEQ ID NO: 5), VDQRMKN (SEQ ID NO: 6), and PQLRGNQ (SEQ ID NO: 7). These substitutions are preferred for achieving a mutant factor VIIIa having a reduced rate of inactivation by activated protein C, but unlike mutants having single mutation replacements of the P1 Arg residue the resulting factor VIIIa is capable of being inactivated by activated protein C.

Suitable mutant factor VIII sequences that can be modified in accordance with the present invention can also include any previously known or subsequently identified mutant factor VIII sequences that have modified properties with regard to various attributes, including, without limitation, antigenicity, circulating half-life, protein secretion, affinity for factor IXa and/or factor X, altered factor VIII-inactivation cleavage sites, enhanced specific activity of factor VIIIa, stability of the activated factor VIIIa form, immunogenicity, and shelf-life.

One example of a suitable mutant factor VIII that can be modified in accordance with the present invention is a factor VIII having a modified calcium binding site, preferably at residue 113 of SEQ ID NO: 2. This affords a factor VIIIa having increased specific activity. Exemplary mutants of this type are described in U.S. patent application Ser. No. 10/581,471 to Fay et al., which is hereby incorporated by reference in its entirety. Preferably, the residue 113 mutant also is modified in accordance with the one or more of the mutations described above (e.g., at positions 333-339).

A second example of a suitable mutant factor VIII that can be modified in accordance with the present invention is a B-domainless factor VIII that contains amino acid residues 1-740 and 1690-2332 of SEQ ID NO: 2 (see, e.g., U.S. Pat. No. 6,458,563 to Lollar, which is hereby incorporated by reference in its entirety).

In one embodiment of the B-domainless recombinant factor VIII of the present invention, the B-domain is replaced by a DNA linker segment and at least one codon is replaced with a codon encoding an amino acid residue that has the same charge as a corresponding residue of porcine factor VIII (see, e.g., U.S. Patent Application Publication No. 2004/0197875 to Hauser et al., which is hereby incorporated by reference in its entirety).

In another embodiment of the B-domainless recombinant factor VIII of the present invention, the modified mutant factor VIII is encoded by a nucleotide sequence having a truncated factor IX intron 1 inserted in one or more locations (see, e.g., U.S. Pat. No. 6,800,461 to Negrier and U.S. Pat. No. 6,780,614 to Negrier, each of which is hereby incorporated by reference in their entirety). This recombinant factor VIII can be used for yielding higher production of the recombinant factor VIII in vitro as well as in a transfer vector for gene therapy (see, e.g., U.S. Pat. No. 6,800,461 to Negrier, which is hereby incorporated by reference in its entirety). In a particular example of this embodiment, the recombinant factor VIII can be encoded by a nucleotide sequence having a truncated factor IX intron 1 inserted in two locations, and having a promoter that is suitable for driving expression in hematopoietic cell lines, and specifically in platelets (see, e.g., U.S. Pat. No. 6,780,614 to Negrier, which is hereby incorporated by reference in its entirety).

Regardless of the embodiment, the B-domainless factor VIII preferably contains one or more of the mutations described above (e.g., at positions 333-339). Recombinant factor VIII proteins prepared in accordance with the Examples herein are B-domainless.

A third example of a suitable mutant factor VIII that can be modified in accordance with the present invention is a chimeric human/animal factor VIII that contains one or more animal amino acid residues as substitution(s) for human amino acid residues that are responsible for the antigenicity of human factor VIII. In particular, animal (e.g., porcine) residue substitutions can include, without limitation, one or more of the following: R484A, R488G, P485A, L486S, Y487L, Y487A, S488A, S488L, R489A, R489S, R490G, L491S, P492L, P492A, K493A, G494S, V495A, K496M, H497L, L498S, K499M, D500A, F501A, P502L, 1503M, L504M, P505A, G506A, E507G, 1508M, 1508A, M21991, F2200L, L2252F, V2223A, K2227E, and/or L2251 (U.S. Pat. No. 5,859,204 to Lollar, U.S. Pat. No. 6,770,744 to Lollar, and U.S. Patent Application Publication No. 2003/0166536 to Lollar, each of which is hereby incorporated by reference in its entirety). Preferably, the recombinant chimeric factor VIII contains one or more of the mutations described above (e.g., at positions 333-339).

A fourth example of a suitable mutant factor VIII that can be modified in accordance with the present invention is a factor VIII that has enhanced affinity for factor IXa (see, e.g., Fay et al., "Factor VIIIa A2 Subunit Residues 558-565 Represent a Factor IXa Interactive Site," *J. Biol. Chem.* 269(32): 20522-7 (1994); Bajaj et al., "Factor IXa: Factor VIIIa Interaction. Helix 330-338 of Factor IXa Interacts with Residues 558-565 and Spatially Adjacent Regions of the A2 Subunit of Factor VIIIa," *J. Biol. Chem.* 276(19):16302-9 (2001); and Lenting et al., "The Sequence Glu1811-Lys1818 of Human Blood Coagulation Factor VIII Comprises a Binding Site for Activated Factor IX," *J. Biol. Chem.* 271(4):1935-40 (1996), each of which is hereby incorporated by reference in their entirety) and/or factor X (see, e.g., Lapan et al., "Localization of a Factor X Interactive Site in the A1 Subunit of Factor VIIIa," *J. Biol. Chem.* 272:2082-88 (1997), which is hereby incorporated by reference in its entirety). Preferably, the enhanced-affinity factor VIII contains one or more of the mutations described above (e.g., at positions 333-339).

A fifth example of a suitable mutant factor VIII that can be modified in accordance with the present invention is a factor VIII that is modified to enhance secretion of the factor VIII (see, e.g., Swaroop et al., "Mutagenesis of a Potential Immunoglobulin-Binding Protein-Binding Site Enhances Secretion of Coagulation Factor VIII," *J. Biol. Chem.* 272(39): 24121-4 (1997), which is hereby incorporated by reference in its entirety). Preferably, the secretion enhanced mutant factor VIII contains one or more of the mutations identified above (e.g., at positions 333-339).

A sixth example of a suitable mutant factor VIII that can be modified in accordance with the present invention is a factor VIII with an increased circulating half-life. This modification can be made using various approaches, including, without limitation, by reducing interactions with heparan sulfate (Sarafanov et al., "Cell Surface Heparan Sulfate Proteoglycans Participate in Factor VIII Catabolism Mediated by Low Density Lipoprotein Receptor-Related Protein," *J. Biol. Chem.* 276(15): 11970-9 (2001), which is hereby incorporated by reference in its entirety) and/or low-density lipoprotein receptor-related protein ("LRP") (Saenko et al., "Role of the Low Density Lipoprotein-Related Protein Receptor in Mediation of Factor VIII Catabolism," *J. Biol. Chem.* 274 (53):37685-92 (1999); and Lenting et al., "The Light Chain of Factor VIII Comprises a Binding Site for Low Density Lipoprotein Receptor-Related Protein," *J. Biol. Chem.* 274(34): 23734-9 (1999), each of which is hereby incorporated by reference in their entirety). Preferably, the half-life enhanced mutant factor VIII contains one or more of the mutations described above (e.g., at positions 333-339).

A seventh example of a suitable mutant factor VIII that can be modified in accordance with the present invention is a modified factor VIII encoded by a nucleotide sequence modified to code for amino acids within known, existing epitopes to produce a recognition sequence for glycosylation at asparagines residues (see, e.g., U.S. Pat. No. 6,759,216 to Lollar, which is hereby incorporated by reference in its entirety). The mutant factor VIII of this example can be useful in providing a modified factor VIII that escapes detection by existing inhibitory antibodies (low antigenicity factor VIII) and which decreases the likelihood of developing inhibitory antibodies (low immunogenicity factor VIII). In one particular embodiment of this example, the modified factor VIII is mutated to have a consensus amino acid sequence for N-linked glycosylation. An example of such a consensus sequence is N-X-S/T, where N is asparagine, X is any amino acid, and S/T stands for serine or threonine (see U.S. Pat. No. 6,759,216 to Lollar, which is hereby incorporated by reference in its entirety). Preferably, the glycosylation site-modified factor VIII contains one or more of the mutations identified above (e.g., at positions 333-339).

An eighth example of a suitable mutant factor VIII that can be modified in accordance with the present invention is a modified factor VIII that is a procoagulant-active factor VIII having various mutations (see, e.g., U.S. Patent Application Publication No. 2004/0092442 to Kaufman et al., which is hereby incorporated by reference in its entirety). One example of this embodiment relates to a modified factor VIII that has been modified to (i) delete the von Willebrand factor binding site, (ii) add a mutation at Arg 740, and (iii) add an amino acid sequence spacer between the A2- and A3-domains, where the amino acid spacer is of a sufficient length so that upon activation, the procoagulant-active factor VIII protein becomes a heterodimer (see U.S. Patent Application Publication No. 2004/0092442 to Kaufman et al., which is hereby incorporated by reference in its entirety). Preferably, procoagulant active factor VIII is also modified to contain one or more of the mutations described above (e.g., at positions 333-339).

Further, the mutant factor VIII can be modified to take advantage of various advancements regarding recombinant coagulation factors generally (see, e.g., Saenko et al., "The Future of Recombinant Coagulation Factors," *J. Thrombosis and Haemostasis* 1:922-930 (2003), which is hereby incorporated by reference in its entirety).

A ninth example of a suitable mutant factor VIII that can be modified in accordance with the present invention is a factor VIII with enhanced stability of both inactivated and activated (factor VIIIa) forms. The enhanced stability factor VIII are characterized by a substitution of one or more charged amino acid residues with a hydrophobic amino acid residue at either or both of the A1:A2 or A2:A3 domain interfaces. Preferred enhanced stability mutant factor VIII include a substitution of the wildtype Glu287 residue, a substitution of the wildtype Asp302 residue, a substitution of the wildtype Asp519 residue, a substitution of the wildtype Glu665 residue, a substitution of the wildtype Glu1984 residue, or combinations thereof. The D302A, E287A, E665A, E665V, D519A, D519V, E1984A, and E1984V substitutions are preferred for achieving a mutant factor VIII that has enhanced stability of both factor VIII and factor VIIIa. This is believed to be achieved by stabilizing the inter-domain interface in factor VIII as well as reduced A2 subunit dissociation from A1/A3C1C2 as compared to wild-type factor VIIIa. These mutant factor VIII forms are described in the simultaneously-filed, co-pending U.S. patent application Ser. No. 12/179,801 to Fay et al., which is hereby incorporated by reference in its entirety. Preferably, the increased stability mutant factor VIII contains one or more of the mutations identified above (e.g., at positions 333-339).

The recombinant factor VIII of the present invention can be modified within a region surrounding an activated protein C cleavage site, as well as be modified to be B-domainless, to be chimeric, to have modified calcium binding sites that enhance factor VIIIa activity (e.g., at position 113), to have altered inactivation cleavage sites, to have enhanced factor IXa and/or factor X affinity, to have enhanced secretion, to have an increased circulating half-life, to have mutant glycosylation sites, to have increased stability; or to possess any two or more of such modifications in addition to the modifications within a region surrounding an activated protein C cleavage site, and a modified calcium-binding site that improves the specific activity of the recombinant factor VIII.

The recombinant factor VIII is preferably produced in a substantially pure form. In a particular embodiment, the substantially pure recombinant factor VIII is at least about 80% pure, more preferably at least 90% pure, most preferably at least 95% pure. A substantially pure recombinant factor VIII can be obtained by conventional techniques well known in the art. Typically, the substantially pure recombinant factor VIII is secreted into the growth medium of recombinant host cells. Alternatively, the substantially pure recombinant factor VIII is produced but not secreted into growth medium. In such cases, to isolate the substantially pure recombinant factor VIII, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure recombinant factor VIII is subjected to gel filtration in an appropriately sized dextran or polyacrylamide column to separate the recombinant factor VIII. If necessary, a protein fraction (containing the substantially pure recombinant factor VIII) may be further purified by high performance liquid chromatography ("HPLC").

Another aspect of the present invention relates to an isolated nucleic acid molecule that encodes the recombinant factor VIII of the present invention. The isolated nucleic acid molecule encoding the recombinant factor VIII can be either RNA or DNA.

In another embodiment, the isolated nucleic acid molecule can have a nucleotide sequence encoding a mutation at position 113 that enhances factor VIIIa activity, as modified with one or more of the substitutions within a region surrounding an activated protein C cleavage site.

In another embodiment, the isolated nucleic acid molecule can have a nucleotide sequence encoding a B-domainless factor VIII of the type described above, as modified with one or more of the substitutions within a region surrounding an activated protein C cleavage site.

In another embodiment, the isolated nucleic acid molecule can have a nucleotide sequence encoding a chimeric human/porcine of the type described above, as modified with one or more of the substitutions within a region surrounding an activated protein C cleavage site.

In another embodiment, the isolated nucleic acid molecule can have a nucleotide sequence encoding a factor VIII whose inactivation sites have been modified as described above, as further modified with one or more of the substitutions within a region surrounding an activated protein C cleavage site.

In yet another embodiment, the isolated nucleic acid molecule can have a nucleotide sequence encoding a factor VIII whose affinity for factor IXa and/or factor X has been enhanced, as further modified with one or more of the substitutions within a region surrounding an activated protein C cleavage site.

In a still further embodiment, the isolated nucleic acid molecule can have a nucleotide sequence encoding a factor VIII whose affinity for various serum-binding proteins has been altered to increase its circulating half-life, as further modified with one or more of the substitutions within a region surrounding an activated protein C cleavage site.

In a further embodiment, the isolated nucleic acid molecule can have a nucleotide sequence encoding a factor VIII that has increased secretion in culture, as further modified with one or more of the substitutions within a region surrounding an activated protein C cleavage site.

In a further embodiment, the isolated nucleic acid molecule can have a nucleotide sequence encoding a factor VIII that possesses one or more non-naturally occurring glycosylation site, as further modified with one or more of the substitutions within a region surrounding an activated protein C cleavage site.

In another embodiment, the isolated nucleic acid molecule can have a substitution of various residues that result in enhanced stability of factor VIII and factor VIIIa (e.g., at positions 287, 302, 579, 665, and/or 1984 described above), as further modified with one or more of the substitutions within a region surrounding an activated protein C cleavage site.

In yet another embodiment, the isolated nucleic acid molecule encodes a recombinant factor VIII that is modified at one or more positions within a region surrounding an activated protein C cleavage site, and is also modified to possess any two or more of the following: modified to be B-domain-less, modified to be chimeric, modified to have altered inactivation cleavage sites, modified to have enhanced factor IXa and/or factor X affinity, modified to have enhanced secretion, modified to have an increased circulating half-life, modified to possess one or more non-naturally occurring glycosylation site, enhanced stability of factor VIII and factor VIIIa, and a modified calcium-binding site that improves activity of the recombinant factor VIII.

Another aspect of the present invention relates to a recombinant DNA expression system that includes an isolated DNA molecule of the present invention, which expression system encodes a recombinant factor VIII. In one embodiment, the DNA molecule is in sense orientation relative to a promoter.

A further aspect of the present invention relates to a host cell including an isolated nucleic acid molecule encoding the recombinant factor VIII of the present invention. In a particular embodiment, the host cell can contain the isolated nucleic acid molecule in the form of a DNA molecule, either as a stable plasmid or as a stable insertion or integration into the host cell genome. In another embodiment, the host cell can contain a DNA molecule in an expression system. Suitable host cells can be, without limitation, animal cells (e.g., baby hamster kidney ("BHK") cells), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), or algal cells.

The recombinant DNA expression system and host cells can be produced using various recombinant techniques well-known in the art, as further discussed below.

The DNA molecule encoding the recombinant factor VIII of the present invention can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements for the transcription and translation of the inserted protein-coding sequences. Thus, one embodiment of the present invention provides a DNA construct containing the isolated nucleic acid of the present invention, which is operably linked to both a 5' promoter and a 3' regulatory region (i.e., transcription terminator) capable of affording transcription and expression of the encoded recombinant factor VIII of the present invention in host cells or host organisms.

With respect to the recombinant expression system of the present invention, an expression vector containing a DNA molecule encoding the recombinant factor VIII of the present invention can be made using common techniques in the art. The nucleic acid molecules of the present invention can be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation.

A variety of host-vector systems may be utilized to express the recombinant factor VIII-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, etc.); insect cell systems infected with virus (e.g., baculovirus); and plant cells infected by bacteria (e.g., *Agrobacterium*). The expression elements of these vectors vary in their strength and specificities. Depending upon the host-vector system utilized, any one of a number of suitable transcription and translation elements can be used.

When recombinantly produced, the factor VIII protein or polypeptide (or fragment or variant thereof) is expressed in a recombinant host cell, typically, although not exclusively, a eukaryote.

Suitable vectors for practicing the present invention include, but are not limited to, the following viral vectors such as lambda vector system gt11, gtWES.tB, Charon 4, and plasmid vectors such as pCMV, pBR322, pBR325, pACYC177, pACYC184, pUC8, pUC9, pUC18, pUC19, pLG339, pR290, pKC37, pKC101, SV40, pBluescript II SK+/− or KS+/− (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology* 185:60-89 (1990), which is hereby incorporated by reference in its entirety), and any derivatives thereof Any appropriate vectors now known or later described for genetic transformation are suitable for use with the present invention.

Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Harbor, N.Y.: Cold Springs Laboratory, (1982), which is hereby incorporated by reference in its entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgamo ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is generally desirable to use strong promoters in order to obtain a high level of transcription and, hence, expression of the gene. Depending upon the host cell system utilized, any one of a number of suitable promoters may be used. For instance, when cloning in *Escherichia coli*, its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, Ipp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one embodiment, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism.

An inducible promoter is a promoter that is capable of directly or indirectly activating transcription of one or more DNA sequences or genes in response to an inducer. In the absence of an inducer, the DNA sequences or genes will not be transcribed.

The DNA construct of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. *Current Protocols in Molecular Biology*, New York, N.Y.: John Wiley & Sons (1989), which are hereby incorporated by reference in their entirety.

As noted, one alternative to the use of prokaryotic host cells is the use of eukaryotic host cells, such as mammalian cells, which can also be used to recombinantly produce the recombinant factor VIII of the present invention. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, and NS-1 cells.

Suitable expression vectors for directing expression in mammalian cells generally include a promoter, as well as other transcription and translation control sequences known in the art. Common promoters include SV40, MMTV, metallothionein-1, adenovirus E1a, CMV, immediate early, immunoglobulin heavy chain promoter and enhancer, and RSV-LTR.

Once the DNA construct of the present invention has been prepared, it is ready to be incorporated into a host cell. Accordingly, another aspect of the present invention relates to a method of making a recombinant cell. Basically, this method is carried out by transforming a host cell with a DNA construct of the present invention under conditions effective to yield transcription of the DNA molecule in the host cell. Recombinant molecules can be introduced into cells via transformation, particularly transduction, conjugation, mobilization, or electroporation.

In view of the recombinant technology discussed herein, another aspect of the present invention relates to a method of making a recombinant factor VIII of the present invention. This method involves growing a host cell of the present invention under conditions whereby the host cell expresses the recombinant factor VIII. The recombinant factor VIII is then isolated. In one embodiment, the host cell is grown in vitro in a growth medium. In a particular embodiment, suitable growth media can include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the recombinant factor VIII. Once the recombinant factor VIII is secreted into the growth medium, it can then be isolated from the growth medium using techniques well-known by those of ordinary skill in the relevant recombinant DNA and protein arts (including those described herein). In another embodiment, the method of making the recombinant factor VIII of the present invention further involves disrupting the host cell prior to isolation of the recombinant factor VIII. In this embodiment, the recombinant factor VIII is isolated from cellular debris.

When an expression vector is used for purposes of in vivo transformation to induce factor VIII expression in a target cell, promoters of varying strength can be employed depending on the degree of enhancement desired. One of skill in the art can readily select appropriate mammalian promoters based on their strength as a promoter. Alternatively, an inducible promoter can be employed for purposes of controlling when expression or suppression of factor VIII is desired. One of skill in the art can readily select appropriate inducible mammalian promoters from those known in the art. Finally, tissue specific mammalian promoters can be selected to restrict the efficacy of any gene transformation system to a particular tissue. Tissue specific promoters are known in the art and can be selected based upon the tissue or cell type to be treated.

Another aspect of the present invention relates to a method of treating an animal for a blood disorder such as hemophilia, particularly hemophilia A. This method involves administering to an animal exhibiting hemophilia A an effective amount of the recombinant factor VIII of the present invention, whereby the animal exhibits effective blood clotting following vascular injury. A suitable effective amount of the recombinant factor VIII can include, without limitation, between about 10 to about 50 units/kg body weight of the animal. The animal can be any mammal, but preferably a human, a rat, a mouse, a guinea pig, a dog, a cat, a monkey, a chimpanzee, an orangutan, a cow, a horse, a sheep, a pig, a goat, or a rabbit.

The recombinant factor VIII of the present invention can be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. In a particular embodiment, the recombinant factor VIII, alone, or in the form of a pharmaceutical composition (i.e., in combination with stabilizers, delivery vehicles, and/or carriers) is infused into patients intravenously according to the same procedure that is used for infusion of human or animal factor VIII.

Alternatively, or in addition thereto, the recombinant factor VIII can be administered by administering a viral vector such as an adeno-associated virus (Gnatenko et al., "Human Factor VIII Can Be Packaged and Functionally Expressed in an Adeno-associated Virus Background: Applicability to Hemophilia A Gene Therapy," *Br. J. Haematol.* 104:27-36 (1999), which is hereby incorporated by reference in its entirety), or by transplanting cells genetically engineered to produce the recombinant factor VIII, typically via implantation of a device containing such cells. Such transplantation typically involves using recombinant dermal fibroblasts, a non-viral approach (Roth et al., "Nonviral Transfer of the Gene Encoding Coagulation Factor VIII in Patients with Sever Hemophilia," *New Engl. J. Med.* 344:1735-1742 (2001), which is hereby incorporated by reference in its entirety).

The treatment dosages of recombinant factor VIII that should be administered to a patient in need of such treatment will vary depending on the severity of the factor VIII deficiency. Generally, dosage level is adjusted in frequency, duration, and units in keeping with the severity and duration of each patient's bleeding episode. Accordingly, the recombinant factor VIII is included in a pharmaceutically acceptable carrier, delivery vehicle, or stabilizer in an amount sufficient to deliver to a patient a therapeutically effective amount of the protein to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of recombinant factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher et al., "Recombinant Factor VIII for the Treatment of Previously Untreated Patients with Hemophilia A—Safety, Efficacy, and Development of Inhibitors," *New Engl. J. Med.* 328:453-459 (1993); Pittman et al., "A2 Domain of Human Recombinant-derived Factor VIII is Required for Procoagulant Activity but not for Thrombin Cleavage," *Blood* 79:389-397 (1992); and Brinkhous et al., "Purified Human Factor VIII Procoagulant Protein: Comparative Hemostatic Response After Infusions into Hemophilic and von Willebrand Disease Dogs," *Proc. Natl. Acad. Sci.* 82:8752-8755 (1985), which are hereby incorporated by reference in their entirety.

Usually, the desired plasma factor VIII activity level to be achieved in the patient through administration of the recombinant factor VIII is in the range of 30-100% of normal. In one embodiment, administration of the therapeutic recombinant factor VIII is given intravenously at a preferred dosage in the range from about 5 to 50 units/kg body weight, and particularly in a range of 10-50 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453-1474, 1460, in *Hematology*, Williams, W. J., et al., ed. (1990), which is hereby incorporated by reference in its entirety. Patients with inhibitors may require a different amount of recombinant factor VIII than their previous form of factor VIII. For example, patients may require less recombinant factor VIII because of its reduced rate of inactivation (and, preferably, higher specific activity than the wild-type VIII and its decreased antibody reactivity). As in treatment with human or plasma-derived factor VIII, the amount of therapeutic recombinant factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed recombinant factor VIII.

Treatment can take the form of a single intravenous administration of the recombinant factor VIII or periodic or continuous administration over an extended period of time, as required. Alternatively, therapeutic recombinant factor VIII can be administered subcutaneously or orally with liposomes in one or several doses at varying intervals of time.

The recombinant factor VIII can also be used to treat uncontrolled bleeding due to factor VIII deficiency in hemophiliacs who have developed antibodies to human factor VIII.

It has been demonstrated herein that the recombinant factor VIII of the present invention can differ in rate of inactivation when compared to the wild-type factor VIII. Factor VIII proteins that retain procoagulant activity for longer duration are useful in treatment of hemophilia because lower dosages will be required to correct a patient's factor VIII deficiency. This will not only reduce medical expense for both the patient and the insurer, but also reduce the likelihood of developing an immune response to the factor VIII (because less antigen is administered).

EXAMPLES

The following examples are provided to illustrate embodiments of the present invention but are by no means intended to limit its scope.

Materials and Methods

Reagents

The monoclonal antibody 58.12, which recognizes the N-terminus of the A1 domain of factor VIII, was a gift from Bayer Corporation (Berkeley, Calif.). The monoclonal antibody R8B12, which recognizes the C-terminus of the A2 domain was obtained from Green Mountain Antibodies (Burlington, Vt.). The C5 antibody was a generous gift from Zaverio Ruggeri. The ESH8 antibody, which recognizes the light chain of factor VIII was obtained from American Diagnostica. Phospholipid vesicles containing 20% PS, 40% PC, and 40% PE were prepared using octylglucoside as described previously (Mimms et al., "Phospholipid Vesicle Formation and Transmembrane Protein Incorporation Using Octyl Glucoside," *Biochemistry* 20:833-840 (1981), which is hereby incorporated by reference in its entirety). The reagents, α-thrombin, factor IXaβ, factor X, and human APC (Enzyme Research Laboratories, South Bend, Ind.), hirudin and phospholipids, (Sigma, St. Louis, Mo.), chromogenic APC substrate S2366 (L-pyroglutamyl-L-prolyl-L-arginine-p-nitroanilide hydrochloride; Chromogenix Instrumentation Laboratory S.p.A, Milano, Italy), chromogenic factor Xa substrate Pefa-5523 ($CH_3OCO$-D-CHA-Gly-Arg-pNA-AcOH; Centerchem, Inc., Norwalk, Conn.) were purchased from the indicated vendors. The B-domainless factor VIII expression vector (HSQ-MSAB-NotI-RENeo) and Bluescript cloning vector (Bluescript II K/S$^-$) were gifts kindly provided by Dr. Pete Lollar and John Healey. Reagents used for cell culture were obtained from Gibco BRL (Gaithesburg, Md.).

Construction, Expression, and Purification of Recombinant Factor VIII Mutants Recombinant factor VIII variants were constructed as B-domainless factor VIII forms, stably transfected into BHK cells, and proteins expressed were purified as described previously. Factor VIII mutants, 336(P4-P3')562, 336(P4-P2) 562, and 336(P1'-P3')562, were prepared by substituting the designated P4-P3' residues surrounding the P1 Arg336 with the corresponding residues surrounding Arg562, whereas 562 (P4-P3')336 and 562(P4-P2)336 mutants were prepared by substituting the P4-P3' residues surrounding Arg562 with the corresponding residues surrounding Arg336. Purified factor VIII proteins were typically >90% pure as judged by SDS-PAGE and staining with GelCode Blue (Pierce, Rockford, Ill.). Specific activity values for these proteins were calculated from activity and concentration values determined by a one-stage clotting assays and ELISA, respectively, as previously described (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety).

Reaction of Factor VIIIa with APC

Factor VIII (130 nM) was activated by addition of 10-20 nM thrombin in 20 mM HEPES pH 7.2, 100 mM NaCl, 5 mM $CaCl_2$, 0.01 % Tween 20, and 100 μg/ml bovine serum albumin (Buffer A) and reactions were run at 37° C. Thrombin was inhibited after 2 min by the addition of 10-20 U/ml hirudin, and the resultant factor VIIIa was reacted with APC (2 or 40 nM) in the presence of 100 μM phospholipid vesicles. Aliquots were removed at the indicated times to assess residual factor VIIIa activity by factor Xa generation assay and proteolysis of subunits by Western blotting. The concentration of factor VIIIa employed represented the approximate Km value for inactivation by APC (~100 nM) (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). Limitations in levels of several of the expressed proteins did not permit use of higher substrate concentrations.

Factor Xa Generation Assay

The rate of conversion of factor X to Xa was monitored in a purified system (Lollar et al., "Factor VIII and Factor VIIIa," *Methods Enzymol.* 222:128-143 (1993), which is hereby incorporated by reference in its entirety). Factor Xa generation was initiated by addition of factor IXa (40 nM) and factor X (400 nM) into the factor VIIIa reaction mixture. Aliquots were removed at appropriate times and added to tubes containing EDTA (50 mM final concentration) to assess initial rates of product formation. Rates of factor Xa generation were determined by the addition of the chromogenic Xa substrate, Pefa-5523 (0.46 mM final concentration). Reactions were read at 405 nm for 5 min using a Vmax microtiter plate reader (Molecular Devices, Sunnyvale, Calif.). Factor VIIIa activity was determined based upon rates of factor Xa generated (nM) per minute, and this information was used to determine the concentration of residual, active factor VIII.

For each data set, control experiments assessing factor VIIIa stability were performed in the absence of APC to determine the rates of factor VIIIa activity loss resulting from A2 subunit dissociation. At the concentrations of factor VIIIa employed, this value approximated a 10% loss of the initial activity over a 20 min time course. Thus, for each time point in the time course experiments including APC, the observed residual activity was corrected for the contribution of activity loss from this APC-independent mechanism. In addition, the correlation of APC concentration to rate of proteolysis (as judged by cleavage of the factor VIIIa A1 subunit by Western blotting, see below) was determined over the range of APC concentrations (from 2 to 40 nM). Deviations from linearity (~2.9 fold) in the A1 subunit cleavage rates observed for 40 nM APC compared to 2 nM APC were used in correcting calculations for inactivation and subunit cleavage rates.

Western Blotting

Aliquots from the APC cleavage reactions were removed at the indicated times and the reactions were stopped with SDS-PAGE buffer. Samples were subjected to SDS-PAGE using 8% acrylamide gels and Western blotting was performed as described previously (Nogami et al., "Thrombin-catalyzed Activation of Factor VIII with His Substituted for Arg372 at the P1 Site," *Blood* 105:4362-4368 (2005), which is hereby incorporated by reference in its entirety). Cleavage at Arg336 was monitored using the 58.12 monoclonal antibody followed by a biotinylated goat anti-mouse secondary antibody, streptavidin and biotinylated alkaline phosphatase (Bio-Rad Laboratories, Hercules, Calif.) to enhance the detection of A1-containing bands. Cleavage at Arg562 was monitored using the R8B12 monoclonal antibody, followed by a goat anti-mouse alkaline phosphatase-linked secondary antibody (Sigma). Signals were detected using the enhanced chemofluorescence system (Amersham Biosciences), and the blots were scanned at 570 nm using Storm 860 (Molecular Devices, Sunnyvale, Calif.). Densitometric scans were quantified from linear density regions of the blots using Image Quant software (Molecular Devices).

Data Analysis

All experiments were performed at least 3 separate times, and average values with standard deviations are shown. The concentration of factor VIIIa generated following reaction of factor VIII with thrombin was calculated from blotting data based upon density values for residual single chain and heavy chain compared with values for A1 and A2 subunits as previously described (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). Typically ~80-85% of factor VIII was converted to factor VIIIa using the conditions described above. Initial time points (where up to ~50% substrate was utilized) were fitted to the second order polynomial equation (Eq. 1) using nonlinear least squares regression analysis, $[FVIIIa]=A+Bt+Ct^2$ (Eq. 1) where [FVIIIa] is factor VIIIa concentration in nM, t is time in minutes, and A, B, and C are coefficients of the quadratic equation. Specifically, A corresponds to the initial concentration of factor VIIIa or A1 or A2 subunit in nM and B corresponds to the slope value at time zero. The absolute value of B represents the rate of factor VIIIa inactivation or the A1 or A2 subunit cleavage that was normalized by APC concentration and expressed in nM FVIIIa/min/nM APC or nM A1 or A2/min/nM APC, respectively.

The inhibition constant (Ki) for 336(P4-P3')562 on APC-catalyzed cleavage of the WT factor VIIIa A1 subunit was determined by fitting the data using nonlinear least squares regression analysis according to a competitive inhibition model (Eq. 2), $v=Vmax\times[WT]/(Km\times(1+[I]/Ki)+[WT])$ (Eq. 2) where v is the initial velocity in nM/min, [WT] is the concentration of WT factor VIIIa A1 subunit in nM, [1] is the concentration of 336(P4-P3')562 factor VIIIa A1 subunit in nM, Km is the Michaelis-Menten constant of WT factor VIIIa for APC which was previously estimated as 102 nM (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety).

Example 1

Characterization of Recombinant Factor VIII 336(P4-P3')562 and 562(P4-P3')336 Mutants It was recently demonstrated that APC-catalyzed cleavages of factor VIIIa at residues Arg336 and Arg562 occur independently with the rate of proteolysis at the former site ~25-fold faster than the latter (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). While substantial evidence implicates the involvement of exosite-directed interactions in the catalytic mechanism of APC, another factor that may contribute to the disparate reaction rates is the influence of residues surrounding the two P1 Arg residues. To examine the roles of these sequences in cofactor cleavage and inactivation, several recombinant B-domainless factor VIII mutants were prepared by replacing the P4-P3' sequence surrounding the faster-reacting Arg336 site with that surrounding the slower-reacting Arg562 site and vice-versa (see Table 1 below). Additional variants representing partial sequence replacements were also prepared. The purified proteins revealed three bands of ~170, ~90 and ~80 kDa as visualized by SDS-PAGE and GelCode Blue staining, which corresponded to the predicted molecular masses of the single chain factor VIII, and heavy chain and light chain of the factor VIII heterodimer, respectively.

TABLE 1

Specific Activity Values of 336(P4-P3')562 and 562(P4-P3')336 factor VIII mutants

| Factor VIII | 336(P4-P3') Sequence | 562(P4-P3') Sequence | Specific Activity (%) |
|---|---|---|---|
| WT | P-Q-L-R-M-K-N (SEQ ID NO: 3) | V-D-Q-R-G-N-Q (SEQ ID NO: 4) | 100 ± 15 |
| 336(P4-P3')562 | **V-D-Q**-R-G-**N-Q** (SEQ ID NO: 5) | | 120 ± 13 |
| 336(P4-P2)562 | **V-D-Q**-R-M-K-N (SEQ ID NO: 6) | | 101 ± 25 |
| 336(P1'-P3')562 | P-Q-L-R-**G-N-Q** (SEQ ID NO: 7) | | 126 ± 27 |
| 562(P4-P3')336 | | **P-Q-L**-R-**M-K-N** (SEQ ID NO: 8) | 0.2 ± 0.1 |
| 562(P4-P2)336 | | **P-Q-L**-R-G-N-Q (SEQ ID NO: 9) | 0.3 ± 0.1 |

WT sequences for the P4-P3' residues flanking Arg336 and Arg562 are indicated using the single letter designation with specific mutations shown in bold typeface. Specific activity values were determined as described in "Materials and Methods" and are presented as a percentage ± standard deviation of the WT value.

Specific activity values measured for the factor VIII mutants yielded similar values for the 336(P4-P3')562, 336 (P4-P2)562 and 336(P1'-P3')562 variants as compared with WT (Table 1), indicating that residues surrounding Arg336 were not critical to cofactor function and that these positions tolerated sequence substitution. However, factor VIII 562(P4-P3')336 and 562(P4-P2)336 mutants revealed specific activity values <1% that of WT (Table 1). This dramatic decrease in specific activity for mutations surrounding Arg562 likely reflected the importance of these residues for factor VIII function inasmuch as residues 558-565 have been identified as comprising a site for interaction with factor IXa (Fay et al., “Factor VIIIa A2 Subunit Residues 558-565 Represent a factor IXa Interactive Site,” *J. Biol. Chem.* 269:20522-20527 (1994), which is hereby incorporated by reference in its entirety). However, all variants demonstrated similar interaction with thrombin that was indistinguishable from that for WT factor VIII, as judged by rates of cleavage of factor VIII and the generation of factor VIIIa subunits. This observation indicates that mutations surrounding Arg562 did not globally affect factor VIII conformation.

Example 2

Inactivation of 336(P4-P3')562 Factor VIIIa Mutants by APC

Purified factor VIII variants (130 nM) were converted to the active factor VIIIa cofactor following thrombin activation. The resultant factor VIIIa was then reacted with indicated levels of APC in the presence of phospholipid vesicles (100 μM) and cofactor activity was monitored over time using a factor Xa generation assay (FIG. 1). Significantly greater concentrations of APC were employed for inactivation experiments involving the mutant factor VIII forms (40 nM APC) compared to that used for WT factor VIIIa (2 nM APC) based upon reduced reactivity for the variants.

The observed rate of spontaneous loss of factor VIIIa activity obtained in the absence of APC was similar for all three 336(P4-P3')562 variants and WT factor VIIIa forms (~10% activity loss at 20 min) and all data obtained in the presence of APC were corrected for the contribution of inactivation due to this APC-independent mechanism as described in above.

The inactivation rates for the set of 336(P4-P3')562 mutants were reduced 6-11 fold compared to WT factor VIIIa (Table 2 below). Rates were determined from the initial time points (up to 5 min) since significant deviation from the fitted curves occurred at more extended time points. The reason for this deviation likely resulted from depletion of substrate factor VIIIa. The extents for these rate reductions resulting from mutation around Arg336 approached the inactivation rate observed when Arg336 was replaced with a non-cleavable Gln residue (Varfaj et al., “Role of P1 Residues Arg336 and Arg562 in the Activated-Protein-C-catalysed Inactivation of Factor VIIIa,” *Biochem. J.* 396:355-362 (2006), which is hereby incorporated by reference in its entirety), suggesting a greater contribution from cleavage at the Arg562 site to overall loss of cofactor activity. These results indicate that residues both N-terminal and C-terminal to Arg336 site contribute to the efficient inactivation of factor VIIIa by APC.

Example 3

APC Cleavage of A1 and A2 Subunits of 336(P4-P3')562 Factor VIIIa Mutants

The above results indicated reduced rates of APC-catalyzed inactivation of the factor VIIIa forms possessing mutations surrounding Arg336. Western blot analysis was performed to determine the rates of APC-catalyzed proteolysis at Arg336 and Arg562 for the 336(P4-P3')562, 336(P4-P2)562 and 336(P1'-P3')562 factor VIIIa variants and correlate these data to rates for factor VIIIa inactivation (FIG. 2). Cleavage at Arg336 within the factor VIIIa A1 subunit and generation of the $A1^{336}$ product (residues 1-336) were detected by monoclonal antibody 58.12, which recognizes the N-terminus of this subunit. Cleavage at Arg562 within the A2 subunit and generation of the $A2_C$ product (residues 563-740) were detected by monoclonal antibody R8B12, which recognizes a discontinuous epitope within the factor VIII A2 domain (Ansong et al., “Epitope Mapping Factor VIII A2 Domain by Affinity-directed Mass Spectrometry: Residues 497-510 and 584-593 Comprise a Discontinuous Epitope for the Monoclonal Antibody R8B12,” *J. Thromb. Haemost.* 4:842-847 (2006), which is hereby incorporated by reference in its entirety). Concentrations of these substrates and products were quantitated based on linear density values determined from densitometry scans of the blots. Results from this analysis indicated that cleavage rates determined for the A1 subunit for the 336 mutants were significantly slower than that of WT factor VIIIa. Both the 336(P4-P2)562 and the 336(P1'-P3')562 mutants showed similar cleavage rates at the A1 site that were reduced ~16 and ~9-fold, respectively, as compared with the WT protein (FIGS. 2A-B, Table 2). However, the rate of cleavage for the A1 subunit of the fully substituted P4-P3' mutant was reduced by ~100-fold relative to WT. These observations indicate residues both N- and C-terminal to this P1 site affect cleavage by APC, with more extensive mutation altering both sides of the scissile bond showing a maximal defect in cleavage rate.

On the other hand, cleavage rates for the A2 subunit in the 336(P4-P2)562 and 336(P1'-P3')562 variants were similar to that of WT (FIGS. 2A, 2C, Table 2) suggesting a normal interaction of APC and cleavage at this site that was unperturbed by mutation at the A1 scissile bond. It was noted that cleavage of the A2 subunit for the 336(P4-P3')562 appeared a few fold slower than that for WT, and the reason(s) for this disparity are not known.

Correlating the proteolysis and activity data suggested that cleavage of the A2 subunit becomes a more dominant mechanism for cofactor inactivation when cleavage at the A1 site is reduced by mutations surrounding Arg336. Separate muta

TABLE 2

Rates of Factor VIIIa WT and 336(P4-P3')562 Mutants Inactivation and A1 and A2 Subunit Cleavages

| Factor VIIIa | Inactivation (nM FVIIIa/min/nM APC) | A1 Cleavage (nM A1/min/nM APC) | A2 Cleavage (nM A2/min/nM APC) |
|---|---|---|---|
| WT | 5.4 ± 0.6 | 9.5 ± 1.9 | 0.2 ± 0.1 |
| 336(P4-P3')562 | 0.8 ± 0.1 | 0.1 ± 0.01 | 0.05 ± 0.02 |
| 336(P4-P2)562 | 0.5 ± 0.04 | 0.6 ± 0.1 | 0.2 ± 0.1 |
| 336(P1'-P3')562 | 0.9 ± 0.1 | 1.1 ± 0.3 | 0.3 ± 0.04 |

Rates of factor VIIIa inactivation, and A1 and A2 subunit cleavages were estimated by nonlinear least squares regression analysis as described above. Data points represent mean ± standard deviation values of at least 3 separate experiments.

tions N- and C-terminal to Arg336 resulted in marked reductions in cleavage at this site while minimally affecting reaction at the A2 site, and overall yielded significant reductions in rates for cofactor inactivation. Overall, these results suggest that P4-P3' residues surrounding Arg336 make a prominent contribution to the mechanism of APC cleavage at Arg336 and cofactor inactivation by this pathway.

Example 4

Inhibition of WT Factor VIIIa A1 Subunit Cleavage by the 336(P4-P3')562 Mutant To determine whether the ~100-fold slower cleavage at Arg336 for the 336(P4-P3')562 factor VIIIa relative to WT resulted from a defect in the affinity of APC for this substrate, the mutant protein was used as an inhibitor of cleavage of the WT factor VIIIa. The rationale for this approach was that if proteinase binding to the mutant were unaffected, then it would efficiently compete with the WT substrate. Furthermore, since the mutant remains essentially uncleaved at the A1 site during a truncated time course, it would serve as an inhibitor of detected cleavage of the WT substrate. For these reactions, WT (130 nM) and the 336(P4-P3')562 mutant (0-200 nM) factor VIII were simultaneously activated by thrombin (20 nM) and then reacted with a low concentration (2 nM) of APC in the presence of phospholipids (100 μM) (FIGS. 3A-F). Using band density values of the A1 substrate (WT and mutant) and $A1^{336}$ product (WT) from Western blotting, cleavage rates were determined and plotted versus concentration of 336(P4-P3')562 factor VIIIa mutant (FIG. 3G). Control experiments showed no detectable cleavage of the mutant protein up to 40 min using these reaction conditions, whereas the WT protein was cleaved by >50% at the 4 min time point (FIGS. 3B, 3A, respectively), thereby validating this approach. An inhibition constant (Ki) for 336(P4-P3')562 of 36±7 nM was determined by fitting these data to a competitive inhibition model and using a Km of 102 nM as previously determined (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). This Ki value was ~3-fold less than the Km for WT substrate indicating the binding of APC to the mutant was not diminished by the altered P4-P3' sequence but modestly enhanced, possibly the result of the reduced reaction rate with this variant. This result is consistent with regions removed from the P4-P3' making a primary contribution to the affinity of APC for factor VIIIa, and furthermore suggests a primary role of the P4-P3' sequence in affecting kcat.

Example 5

APC Cleavage of A1 and A2 Subunits of 562(P4-P3')336 Factor VIIIa Mutants

Although mutation within the P4-P3' region of Arg562 yielded factor VIII forms lacking cofactor activity, likely due to alteration within a critical factor IXa-interactive site, these reagents could be evaluated as substrates for proteolysis by APC. Thus, a series of experiments was performed to assess the effects of replacing residues around the P1 Arg562 with those that surround the more rapidly cleaved Arg336 site. Western blot analysis was performed to determine the rates of APC-catalyzed proteolysis within the A1 and A2 subunits for two variants, 562(P4-P3')336 and 562(P4-P2)336 factor VIIIa forms (FIG. 4A). Reactions were run using similar conditions as described above and cleavage rates were determined following Western blotting. Cleavage rates of the A1 subunit for both the A2 mutants were similar to that of WT factor VIIIa (FIGS. 4A, 4B, Table 3). This result was consistent with loss of activity due to mutation not resulting from changes in the gross factor VIII conformation, but rather restricted to an altered interactive site in and around Arg562. It was observed that the rate of A2 subunit cleavage for 562(P4-P3')336 mutant was increased ~4 fold, whereas the A2 cleavage rate for 562(P4-P2)336 mutant was similar to that of WT (FIGS. 4A, 4C, Table 3). These results suggested that P4-P3' residues surrounding the Arg562 site make a generally minor contribution to APC-catalyzed cleavage at this site in factor VIIIa.

TABLE 3

Rates of A1 and A2 Subunit Cleavages for WT and 562(P4-P3')336 factor VIIIa/VIII Mutants

| Factor VIIIa/VIII | A1 Cleavage (nM A1/min/nM APC) | A2 Cleavage (nM A2/min/nM APC) |
|---|---|---|
| WT FVIIIa | 8.5 ± 1.8 | 0.5 ± 0.2 |
| 562(P4-P3')336 FVIIIa | 7.3 ± 1.5 | 1.9 ± 0.5 |
| 562(P4-P2)336 FVIIIa | 7.4 ± 1.6 | 0.7 ± 0.2 |
| WT FVIII | | 0.1 ± 0.06 |
| 562(P4-P3')336 FVIII | | 2.7 ± 0.7 |
| 562(P4-P2)336 FVIII | | 0.6 ± 0.3 |

Rates of factor VIIIa/VIII A1 and A2 subunit/domain cleavages were estimated by nonlinear least squares regression analysis as described above. Data points represent mean ± standard deviation values of at least 3 separate experiments.

Example 6

APC Cleavage of A1 and A2 Subunits of 562(P4-P3')336 Factor VIII Mutants

Cleavage of the A2 subunit in factor VIIIa is of apparent secondary importance to cofactor inactivation as compared with cleavage at the A1 site based on the significantly slower rate at this site (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). Furthermore, assessing the rate for cleavage within the A2 subunit is complicated by the tendency for this subunit to dissociate from factor VIIIa, and earlier results have indicated that free A2 subunit is a poor substrate for cleavage by APC (Fay et al., "Activated Protein C-catalyzed Inactivation of Human Factor VIII and Factor VIIIa: Identification of Cleavage Sites and Correlation of Proteolysis with Cofactor Activity," *J. Biol. Chem.* 266:20139-20145 (1991), which is hereby incorporated by reference in its entirety). To better assess contributions of the P4-P3' residues surrounding Arg562 to cleavage at this site, the APC-catalyzed proteolysis of Arg336 and Arg562 in the heavy chain of the factor VIII procofactor for the WT and variant proteins was examined. Use of this substrate stabilizes the inter-domain interactions involving A2 since the A1 and A2 domains are contiguous. Purified factor VIII (130 nM) was reacted with 2 nM APC in the presence of phospholipid vesicles (100 μM) and subsequently subjected to SDS-PAGE and Western blot analysis. Cleavage of factor VIII at Arg336 generates the $A1^{336}$ fragment (residues 1-336) that is reactive with the 58.12 antibody and the rate of appearance of this fragment was similar in the WT and the two mutants (FIGS. 5A, 5B, Table 3). Inasmuch as APC rapidly attacks Arg740 in factor VIII (Fay et al., "Activated Protein C-catalyzed Inactivation of Human Factor VIII and Factor VIIIa: Identification of Cleavage Sites and Correlation of Proteolysis with Cofactor Activity," *J. Biol. Chem.* 266: 20139-20145 (1991), which is hereby incorporated by reference in its entirety), cleavage at Arg562 in the procofactor was monitored by the rate of appearance of the terminal product, the A2c fragment (residues 563-740), which is reactive with R8B12 antibody. Rates of generation of this fragment were 27-fold and 6-fold greater for 562(P4-P3')336 and 562(P4-P2)336 mutant factor VIII forms, respectively, compared with WT factor VIII (FIGS. 5A, 5C, Table 3). These results indicated that the P4-P3' residues surrounding Arg562 indeed influence the mechanism for catalysis at this site in the factor VIII procofactor by APC and that replacement of residues at both N- and C-terminal positions relative to the P1 Arg with residues that appear more optimal for this interaction facilitate the cleavage reaction.

Western blotting of the factor VIII digest time course with the anti-A2 domain monoclonal antibody revealed two intermediates. One fragment of slightly greater mass (~48 kDa) than the A2 subunit and representing factor VIII residues 337-740 was predicted based upon cleavage at Arg336. Cleavage at this site generated the $A1^{336}$ fragment indicated in the blots with the anti-A1 specific monoclonal antibody. However, a second, slightly smaller fragment (~43 kDa) was also noted. This band was of similar size to the A2 subunit (residues 373-740) derived from thrombin cleavage of factor VIII. Control experiments indicated that this fragment did not react with C5 antibody, which recognizes an epitope within residues 351-365 (Foster et al., "Localization of the Binding Regions of a Murine Monoclonal Anti-Factor VIII Antibody and a Human Anti-factor VIII Alloantibody, Both of which Inhibit Factor VIII Procoagulant Activity, to Amino Acid Residues Threonine351-Serine365 of the Factor VIII Heavy Chain," *J. Clin. Invest.* 82:123-128 (1988), which is hereby incorporated by reference in its entirety), whereas the 48-kDa band did, confirming its origin. Furthermore, the 43-kDa band was not present following reaction of APC with a factor VIII variant possessing an Arg372Gln mutation, which would preclude cleavage at residue 372. Taken together, these results suggest APC catalyzes limited attack at Arg372 in the factor VIII procofactor.

The A1 subunit cleavage in the factor VIII procofactor does not comply with the second order kinetics (FIG. 5B). The reason(s) for this is (are) not clear but may suggest a more complex mechanism involved in $A1^{336}$ product generation as a result of cleavage at both Arg336 and Arg372 with concomitant subsequent cleavage at Arg336, the latter as judged by little or no intact A1 subunit observed in the blots. However, comparison of the amounts of $A1^{336}$ product released indicates minimal differences between the two mutants and WT factor VIII.

Discussion of Examples 1-6

In the above Examples, the role of residues surrounding the two P1Arg residues attacked by APC during inactivation of factor VIIIa was assessed. The rationale for this study was based upon the earlier observations indicating that proteolysis of these sites in the cofactor occurred independently and that Arg336 was cleaved at a rate ~25-fold greater than that observed for cleavage at Arg562 (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). Results obtained evaluating rates of cleavage where selected P4-P3' residues for one site were replaced with residues from the complementary site indicated that rapid cleavage at Arg336 resulted from favorable P4-P3' residues surrounding this site since replacement of residues 333-339 with residues 559-565 yielded significantly diminished rates of cleavage. Conversely, the relatively slower rate of cleavage at Arg562 could be modestly accelerated following replacement of residues 559-565 with residues 333-339.

The wild type-like specific activity of factor VIII forms possessing mutations at P4-P3' residues surrounding Arg336 indicated that these residues are not critical to factor VIIIa cofactor function. This observation is supported by the absence of point mutations in the Hemophilia A database over this region that yield a hemophilic phenotype (with the exception of mutation to stop codons), as well as no reports in the literature of this site representing an interactive region for procoagulant macromolecules. In contrast, the P4-P3' residues flanking Arg562 revealed a crucial role in factor VIIIa cofactor activity as judged by marked reductions in specific activity when replaced. These observations were consistent with residues 558-565 serving as a factor IXa interactive site (Fay et al., "Factor VIIIa A2 Subunit Residues 558-565 Represent a factor IXa Interactive Site," *J. Biol. Chem.* 269: 20522-20527 (1994), which is hereby incorporated by reference in its entirety). Indeed, the missense mutations Ser558Phe, Val559Ala, Val560Ala, Asn564Ser, and Gln565Arg have been reported as yielding hemophilic phenotypes of varying severity (Kemball-Cook et al., "The Factor VIII Mutation Database on the World Wide Web: The Haemophilia A Mutation, Search, Test and Resource Site," Nucleic Acids Res. 25:128-132 (1997), which is hereby incorporated by reference in its entirety). Recapitulating four of these point mutations in recombinant factor VIII expressed in heterologous mammalian cells for in vitro functional analyses demonstrated a significant reduction in the kcat values for factor IXa-catalyzed generation of factor Xa without appreciably affecting the affinity of factor VIIIa for factor IXa (Jenkins et al., "Mutations Associated with Hemophilia A in the 558-565 Loop of the Factor VIIIa A2 Subunit Alter the Catalytic Activity of the Factor Xase Complex," *Blood* 100: 501-508 (2002), which is hereby incorporated by reference in its entirety).

The above Examples demonstrate that replacement of selected P4-P3' residues surrounding the faster-reacting Arg336 with those from the slower-reacting Arg562 results in up to an ~100-fold reduction in the rate of cleavage at that site. This reduced rate in cleavage at the P1 Arg336 residue was derived from alteration of both the N-and C-terminal residues adjacent to the scissile bond inasmuch as replacement of either P4-P2 or P1'-P3' residues yielded factor VIIIa variants showing ~9-16 fold reductions in cleavage rate. These observations suggest an apparent synergy when both the prime and non-prime residues were altered. The rates in APC-catalyzed factor VIIIa inactivation for these variants were of similar magnitude to those determined in a prior study where Arg336 was replaced with Ala or Gln, which resulted in essentially no observed cleavage at the Arg336 site (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). Thus, proteolysis at Arg562 in the A2 subunit now contributes more heavily to the overall mechanism of cofactor inactivation.

Assessing APC-catalyzed proteolysis directed towards the A2 subunit in factor VIIIa is problematic due to the tendency for this subunit to dissociate and the earlier observation that the free A2 subunit is not efficiently cleaved by APC (Fay et al., "Activated Protein C-catalyzed Inactivation of Human Factor VIII and Factor VIIIa: Identification of Cleavage Sites and Correlation of Proteolysis with Cofactor Activity," *J. Biol. Chem.* 266:20139-20145 (1991), which is hereby incorporated by reference in its entirety). Although the factor VIII heterodimer is a poorer substrate for APC than the factor VIIIa cofactor, as judged by reduced rates of cleavage at both the A1 and A2 sites, it does have the advantage of presenting the A2 domain as contiguous with A1, and in this regard approximates the structure of the factor Va heavy chain. Evaluation of both factor VIII and factor VIIIa substrates revealed that replacing residues 559-565 with residues 333-339 resulted in enhanced cleavage rates at the A2 site. The significantly greater effect on cleavage at Arg562 observed for the procofactor form may be attributed to structural differences surrounding the scissile bond. Taken together with the above results, these data indicate residues flanking the P1 Arg336 as being more optimal for engaging the APC active site than those flanking the P1 Arg562.

APC-catalyzed inactivation of the homologous cofactor, factor Va, also results from cleavage at two sites in the protein with initial cleavage at Arg506 in the A2 domain preceding appreciable cleavage at Arg306 within the A1 domain 26). However, this cleavage order appears to be dictated in large part by conformational effects. Since the A1 and A2 domains are contiguous in factor Va, it is speculated that initial cleavage at Arg506 is required to expose the more cryptic P1 Arg306. This hypothesis is supported by the thrombophilic mutation Arg506Gln, that results in a further reduction in the rate of cleavage at the 306 site compared to the WT protein (Kalafatis et al., "Biochemical Prototype for Familial Thrombosis: A Study Combining a Functional Protein C Mutation and Factor V Leiden," *Arterioscler. Thromb. Vasc. Biol.* 15:2181-2187 (1995), which is hereby incorporated by reference in its entirety).

Little information is available regarding optimal residues and critical positions flanking the scissile bond for catalysis by APC. In an earlier study, P3-P3' residues of the serpin antithrombin III were replaced by the P3-P3' residues surrounding the Arg506 cleavage site in factor Va and resulted in an ~100-fold increase in serpin reactivity toward APC (Rezaie, "Insight into the Molecular Basis of Coagulation Proteinase Specificity by Mutagenesis of the Serpin Antithrombin," *Biochemistry* 41:12179-12185 (2002), which is hereby incorporated by reference in its entirety). The author concluded that the P3-P3' residues in factor Va conferred specificity for APC by establishing the transition state of the enzyme-substrate complex and consequently accelerating catalysis. That study also presented data showing that sole substitution of Gly with Arg at the P2 site accounted for an ~40-fold increase in catalytic rate, indicating the importance of this residue in engaging the APC active site. Examination of the APC crystal structure reveals a more open and polar S2 pocket than in thrombin or factor Xa that is probably due to the presence of Thr at position 99, which has a shorter side chain than that of Leu in thrombin and Tyr in factor Xa (Mather et al., "The 2.8 A Crystal Structure of Gla-domainless Activated Protein C," *EMBO J.* 15:6822-6831(1996), which is hereby incorporated by reference in its entirety). The open S2 pocket might explain the various P2 residues (Arg, Thr, Leu, and Gln) accommodated in the factor Va and factor VIIIa substrates (Mather et al., "The 2.8 A Crystal Structure of Gla-domainless Activated Protein C," *EMBO J.* 15:6822-6831 (1996), which is hereby incorporated by reference in its entirety). Furthermore, APC appears to contrast other homologous proteinases in that specificity sites possess a more polar character and may show preference for basic residues at P2 and P3' (Bode et al., "Comparative Analysis of Haemostatic Proteinases: Structural Aspects of Thrombin, Factor Xa, Factor IXa and Protein C," *Thromb. Haemost.* 78:501-511 (1997), which is hereby incorporated by reference in its entirety). While factor Va contains a P2Arg adjacent to P1 Arg506 and a P3'Lys adjacent to P1 Arg306, basic residues at these positions are absent in factor VIII. Overall, the restricted number of physiologic substrates and the lack of sequence consensus at the P4-P3' positions make it difficult to identify an optimal sequence for cleavage catalyzed by APC.

Despite the effects of these flanking residues on catalysis, earlier results have shown that primary binding interactions between APC and the factor VIII substrates are exosite dependent (Manithody et al., "Exosite-dependent Regulation of Factor VIIIa by Activated Protein C," *Blood* 101:4802-4807 (2003), which is hereby incorporated by reference in its entirety). Further support for this conclusion was obtained from the competition experiment where it was shown that the factor VIIIa variant 336(P4-P3')562 effectively competed with the WT factor VIIIa for APC. This result showed essentially no contribution from the sequence surrounding the more prominent scissile bond to forming the enzyme-substrate complex, and was reminiscent of the earlier observations by Orcutt et al. (Orcutt et al., "Extended Interactions with Prothrombinase Enforce Affinity and Specificity for its Macromolecular Substrate," *J. Biol. Chem.* 277:46191-46196 (2002), which is hereby incorporated by reference in its entirety), where replacement of the P1-P3 residues in prethrombin 2 yielded significant reductions in Vmax values for activation catalyzed by factor Xa or prothrombinase, but did not impact the affinity of substrate for enzyme. It was observed previously that a double P1 mutant factor VIIIa where the Arg336 and Arg562 were replaced with a non-cleavable Gln also effectively competed with WT factor VIIIa for APC with a Ki value ~10 nM (Varfaj et al., "Role of P1 Residues Arg336 and Arg562 in the Activated-Protein-C-catalysed Inactivation of Factor VIIIa," *Biochem. J.* 396:355-362 (2006), which is hereby incorporated by reference in its entirety). In the above examples a Ki value ~36 nM for the factor VIIIa variant 336(P4-P3')562 was calculated, which is highly resistant to cleavage at Arg336. The somewhat higher affinity of the former "inhibitor" for APC may reflect its full resistance to cleavage compared with the limited resistance of the latter.

In summary, these results demonstrate a primary role for flanking sequences of the P1 sites in modulating rates of inactivation of factor VIIIa by a direct contribution to APC active site engagement. While the sequence surrounding Arg562 is important for cofactor function, thus precluding alteration at this site, mutagenesis at the faster-reacting Arg336 site appears refractory to specific activity concerns and could yield a mechanism to fine tune reductions in the rate of APC-catalyzed cofactor inactivation by selective mutation at this site.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A recombinant factor VIII comprising an A1 domain comprising one or more substitutions within the amino acid sequence EEPQLRMKNNE (residues 331-341 of SEQ ID NO: 2), wherein the one or more substitutions exclude the arginine residue and said recombinant factor VIII has a reduced rate of inactivation by activated protein C compared to wildtype factor VIII.

2. The recombinant factor VIII according to claim 1, wherein the one or more substitutions comprises substitution of proline at the third residue of said amino acid sequence.

3. The recombinant factor VIII according to claim 1, wherein the one or more substitutions comprises substitution of glutamine at the fourth residue of said amino acid sequence.

4. The recombinant factor VIII according to claim 1, wherein the one or more substitutions comprises substitution of leucine at the fifth residue of said amino acid sequence.

5. The recombinant factor VIII according to claim 1, wherein the one or more substitutions comprises substitution of methionine at the seventh residue of said amino acid sequence.

6. The recombinant factor VIII according to claim 1, wherein the one or more substitutions comprises substitution of lysine at the eighth residue of said amino acid sequence.

7. The recombinant factor VIII according to claim 1, wherein the one or more substitutions comprises substitution of asparagine at the ninth residue of said amino acid sequence.

8. The recombinant factor VIII according to claim 1, wherein the one or more substitutions comprise substitution of -PQL- with -VDQ-, substitution of -MKN-with -GNQ- , or both, within said amino acid sequence.

9. The recombinant factor VIII according to claim 1, wherein the recombinant factor VIII consists of domains A1, A2, A3, C1, and C2, or portions thereof.

10. The recombinant factor VIII according to claim 1, wherein the recombinant factor VIII is substantially pure.

11. The recombinant factor VIII according to claim 1 further comprising a point mutation of a glutamic acid residue corresponding to position 113 of SEQ ID NO: 2 (Glu113).

12. A pharmaceutical composition comprising the recombinant factor VIII according to claim 1.

13. The pharmaceutical composition according to claim 12 further comprising a stabilizer, a delivery vehicle, or a pharmaceutically acceptable carrier.

14. A method of treating an animal for hemophilia A, the method comprising:

administering to an animal exhibiting hemophilia A an effective amount of the recombinant factor VIII according to claim 1, whereby the animal exhibits effective blood clotting following vascular injury.

15. The method according to claim 14, wherein the effective amount comprises between about 10 to about 50 units/kg body weight of the animal.

16. The method according to claim 14, wherein the animal is a human.

17. The method according to claim 14, further comprising periodically repeating said administering.

18. The recombinant factor VIII according to claim 1 wherein the recombinant factor VIII further comprises a substitution of a glutamic acid residue corresponding to position 287 of SEQ ID NO: 2(G1u287), a substitution of an aspartic acid residue corresponding to position 302 of SEQ ID NO: 2 (Asp302), a substitution of an aspartic acid residue corresponding to position 519 of SEQ ID NO: 2 (Asp519), a substitution of a glutamic acid residue corresponding to position 665 of SEQ ID NO: 2 (G1u665), a substitution of a glutamic acid residue corresponding to position 1984 of SEQ ID NO: 2 (G1u1984), or combinations thereof.

19. The recombinant factor VIII according to claim 18, wherein the substitution of the Asp302 residue is Asp302Ala.

20. The recombinant factor VIII according to claim 18, wherein the substitution of the G1u287 residue is Glu287Ala.

21. The recombinant factor VIII according to claim 18, wherein the substitution of the G1u665 residue is Glu665Ala or Glu665Val.

22. The recombinant factor VIII according to claim 18, wherein the substitution of the Asp519 residue is Asp519Ala or Asp519Val.

23. The recombinant factor VIII according to claim 18, wherein the substitution of the G1u1984 residue is Glu1984Ala or Glu1984Val.

* * * * *

UNITED STATES PATENT AND TRADEMARK OFFICE

CERTIFICATE OF CORRECTION

PATENT NO. : 8,183,345 B2
APPLICATION NO. : 12/179951
DATED : May 22, 2012
INVENTOR(S) : Philip J. Fay, Hironao Wakabayashi and Fatbardha Varfaj It is certified that error appears in the above-identified patent and that said Letters Patent is hereby corrected as shown below:

In claim 18, at col. 54, line 30, delete "2(G1u287)" and insert --2 (Glu287)--.
In claim 18, at col. 54, line 35, delete "(G1u665)" and insert --(Glu665)--.
In claim 18, at col. 54, line 37, delete "(G1u1984)" and insert --(Glu1984)--.
In claim 20, at col. 54, line 41, delete "G1u287" and insert --Glu287--.
In claim 21, at col. 54, line 43, delete "G1u665" and insert --Glu665--.
In claim 23, at col. 54, line 49, delete "G1u1984" and insert --Glu1984--.

Signed and Sealed this
Tenth Day of July, 2012

David J. Kappos
*Director of the United States Patent and Trademark Office*